(12) United States Patent
Kaplan et al.

(10) Patent No.: US 11,399,842 B2
(45) Date of Patent: Aug. 2, 2022

(54) DEVICES AND METHODS FOR EXCLUDING THE LEFT ATRIAL APPENDAGE

(71) Applicant: Conformal Medical, Inc., Nashua, NH (US)

(72) Inventors: Aaron V. Kaplan, Northwich, VT (US); David Melanson, Hudson, NH (US); Carol Devellian, Topsfield, MA (US); Andy H. Levine, Newton Highlands, MA (US); Andres Chamorro, Ashland, MA (US)

(73) Assignee: Conformal Medical, Inc., Nashua, NH (US)

( * ) Notice: Subject to any disclaimer, the term of this patent is extended or adjusted under 35 U.S.C. 154(b) by 0 days.

(21) Appl. No.: 16/846,076

(22) Filed: Apr. 10, 2020

(65) Prior Publication Data
US 2020/0305889 A1 Oct. 1, 2020
US 2022/0192676 A9 Jun. 23, 2022

Related U.S. Application Data

(63) Continuation of application No. 15/290,692, filed on Oct. 11, 2016, now Pat. No. 10,617,425, which is a
(Continued)

(51) Int. Cl.
A61B 17/12 (2006.01)
A61B 17/00 (2006.01)
(Continued)

(52) U.S. Cl.
CPC .... A61B 17/12122 (2013.01); A61B 17/1215 (2013.01); A61B 17/12145 (2013.01);
(Continued)

(58) Field of Classification Search
CPC .......... A61B 17/0057; A61B 17/00575; A61B 17/00579; A61B 17/00584;
(Continued)

(56) References Cited

U.S. PATENT DOCUMENTS 3,063,453 A 11/1962 Brecht
3,712,305 A 1/1973 Wennerblom et al.
(Continued)

FOREIGN PATENT DOCUMENTS

CA 1341519 2/2007
CN 102088927 6/2011
(Continued)

OTHER PUBLICATIONS

Möbius-Winkler, S., Sandri, M., Mangner, N., Lurz, P., Dähnert, I., Schuler, G. The Watchman Left Atrial Appendage Closure Device for Atrial Fibrillation. J. Vis. Exp. (60), e3671, DOI : 10.3791/3671 (Feb. 28, 2012).
(Continued)

Primary Examiner — Wade Miles
Assistant Examiner — Kankindi Rwego
(74) Attorney, Agent, or Firm — Knobbe Martens Olson & Bear, LLP

(57) ABSTRACT

Devices and methods are described for occluding the left atrial appendage (LAA) to exclude the LAA from blood flow to prevent blood from clotting within the LAA and subsequently embolizing, particularly in patients with atrial fibrillation. An implant is delivered via transcatheter delivery into the LAA. The implant includes a conformable structure comprising a foam body and internal support. The support includes anchors that penetrate the foam body and anchor the implant to the walls of the LAA. The implant provides compliance such that it conforms to the native configuration of the LAA.

20 Claims, 33 Drawing Sheets

Related U.S. Application Data continuation-in-part of application No. 14/203,187, filed on Mar. 10, 2014, now Pat. No. 9,943,315.

(60) Provisional application No. 62/240,124, filed on Oct. 12, 2015.

(51) Int. Cl.
*A61B 17/22* (2006.01)
*A61B 90/00* (2016.01)

(52) U.S. Cl.
CPC .. *A61B 17/12159* (2013.01); *A61B 17/12172* (2013.01); *A61B 17/12177* (2013.01); *A61B 17/12181* (2013.01); *A61B 17/00491* (2013.01); *A61B 17/12136* (2013.01); *A61B 2017/00495* (2013.01); *A61B 2017/1205* (2013.01); *A61B 2017/22038* (2013.01); *A61B 2017/22048* (2013.01); *A61B 2090/064* (2016.02)

(58) Field of Classification Search
CPC ........ A61B 17/00588; A61B 17/00597; A61B 17/0061; A61B 17/00632; A61B 17/00637; A61B 17/00641; A61B 17/12022; A61B 17/12027; A61B 17/12031; A61B 17/12036; A61B 17/1204; A61B 17/12122; A61B 17/12145; A61B 17/1215; A61B 17/12159; A61B 17/12172; A61B 17/12177; A61B 17/12181; 2017/1205; A61B 2017/22038; A61B 2017/22048; A61B 2090/064; A61B 17/00491; A61B 17/12136; A61B 2017/00495
USPC ......................................... 606/194, 200, 213
See application file for complete search history.

(56) References Cited

U.S. PATENT DOCUMENTS

| | | | |
|---|---|---|---|
| 3,812,856 A | 5/1974 | Duncan et al. |
| 3,978,855 A | 9/1976 | McRae et al. |
| 4,061,145 A | 12/1977 | DesMarais |
| 4,475,911 A | 10/1984 | Gellert |
| 5,192,301 A | 3/1993 | Kamiya et al. |
| 5,456,693 A | 10/1995 | Conston et al. |
| 5,634,936 A | 6/1997 | Linden et al. |
| 5,670,572 A | 9/1997 | Ott et al. |
| 5,725,568 A | 3/1998 | Hastings |
| 5,792,179 A | 8/1998 | Sideris |
| 5,823,198 A | 10/1998 | Jones et al. |
| 5,847,012 A | 12/1998 | Shalaby et al. |
| 5,848,040 A | 12/1998 | Tanaka |
| 5,861,003 A | 1/1999 | Latson et al. |
| 5,865,791 A | 2/1999 | Whayne et al. |
| 5,969,000 A | 10/1999 | Yang et al. |
| 5,968,091 A | 11/1999 | Pinchuk |
| 6,152,144 A | 11/2000 | Lesh et al. |
| 6,162,168 A | 12/2000 | Schweich et al. |
| 6,231,561 B1 | 5/2001 | Frazier et al. |
| 6,290,674 B1 | 9/2001 | Roue et al. |
| 6,398,758 B1 | 6/2002 | Jacobsen et al. |
| 6,408,981 B1 | 6/2002 | Smith et al. |
| 6,419,669 B1 | 7/2002 | Frazier et al. |
| 6,423,252 B1 | 7/2002 | Chun et al. |
| 6,436,088 B2 | 8/2002 | Frazier et al. |
| 6,447,539 B1 | 9/2002 | Nelson et al. |
| 6,458,100 B2 | 10/2002 | Roue et al. |
| 6,551,303 B1 | 4/2003 | VanTassel et al. |
| 6,623,450 B1 | 9/2003 | Dutta |
| 6,641,557 B1 | 11/2003 | Frazier et al. |
| 6,651,303 B1 | 11/2003 | Toivanen et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | VanTassel et al. |
| 6,712,804 B2 | 3/2004 | Roue et al. |
| 6,712,810 B2 | 3/2004 | Harrington et al. |
| 6,723,108 B1 | 4/2004 | Jones et al. |
| 6,730,108 B2 | 5/2004 | Van Tassel et al. |
| 6,881,875 B2 | 4/2005 | Swenson |
| 6,941,169 B2 | 9/2005 | Pappu |
| 6,949,113 B2 | 9/2005 | Van Tassel et al. |
| 6,977,323 B1 | 12/2005 | Swenson |
| 6,979,344 B2 | 12/2005 | Jones et al. |
| 6,994,092 B2 | 2/2006 | Van Der et al. |
| 7,011,671 B2 | 3/2006 | Welch |
| 7,044,134 B2 | 5/2006 | Khairkhahan et al. |
| 7,056,294 B2 | 6/2006 | Khairkhahan et al. |
| 7,115,110 B2 | 10/2006 | Frazier et al. |
| 7,128,073 B1 | 10/2006 | Van der Burg et al. |
| 7,152,605 B2 | 12/2006 | Khairkhahan et al. |
| 7,169,164 B2 | 1/2007 | Borillo et al. |
| 7,192,439 B2 | 3/2007 | Khairkhahan et al. |
| 7,226,458 B2 | 6/2007 | Kaplan et al. |
| 7,291,382 B2 | 11/2007 | Krueger et al. |
| 7,293,562 B2 | 11/2007 | Malecki |
| 7,318,829 B2 | 1/2008 | Kaplan et al. |
| 7,344,543 B2 | 3/2008 | Sra |
| 7,358,282 B2 | 4/2008 | Krueger et al. |
| 7,427,279 B2 | 9/2008 | Frazier et al. |
| 7,549,983 B2 | 6/2009 | Roue et al. |
| 7,566,336 B2 | 7/2009 | Corcoran et al. |
| 7,597,704 B2 | 10/2009 | Frazier et al. |
| 7,695,425 B2 | 4/2010 | Schweich et al. |
| 7,713,282 B2 | 5/2010 | Frazier et al. |
| 7,722,641 B2 | 5/2010 | Van Der et al. |
| 7,727,189 B2 | 6/2010 | VanTassel et al. |
| 7,735,493 B2 | 6/2010 | van der Burg et al. |
| 7,747,047 B2 | 6/2010 | Okerlund et al. |
| 7,780,683 B2 | 8/2010 | Roue et al. |
| 7,803,395 B2 | 9/2010 | Datta et al. |
| 7,824,397 B2 | 11/2010 | Mcauley |
| 7,922,716 B2 | 4/2011 | Malecki et al. |
| 7,972,359 B2 | 7/2011 | Kreidler |
| 7,998,138 B2 | 8/2011 | Mcauley |
| 8,043,329 B2 | 10/2011 | Khairkhahan et al. |
| 8,052,715 B2 | 11/2011 | Quinn et al. |
| 8,057,530 B2 | 11/2011 | Kusleika et al. |
| 8,080,032 B2 | 12/2011 | van der Burg et al. |
| 8,097,015 B2 | 1/2012 | Devellian |
| 8,142,470 B2 | 3/2012 | Quinn et al. |
| 8,157,818 B2 | 4/2012 | Gartner et al. |
| 8,197,496 B2 | 6/2012 | Roue et al. |
| 8,197,527 B2 | 6/2012 | Borillo et al. |
| 8,221,445 B2 | 7/2012 | Van Tassel et al. |
| 8,262,694 B2 | 9/2012 | Widomski et al. |
| 8,287,563 B2 | 10/2012 | Khairkhahan et al. |
| 8,313,504 B2 | 11/2012 | Do et al. |
| 8,323,309 B2 | 12/2012 | Khairkhahan et al. |
| 8,337,487 B2 | 12/2012 | Datta et al. |
| 8,361,111 B2 | 1/2013 | Widomski et al. |
| 8,460,282 B2 | 6/2013 | Mcauley |
| 8,480,708 B2 | 7/2013 | Kassab et al. |
| 8,523,897 B2 | 9/2013 | Van Der et al. |
| 8,535,343 B2 | 9/2013 | Van Der et al. |
| 8,540,760 B2 | 9/2013 | Paul, Jr. et al. |
| 8,603,108 B2 | 12/2013 | Roue et al. |
| 8,636,764 B2 | 1/2014 | Miles et al. |
| 8,690,911 B2 | 1/2014 | Miles et al. |
| 8,647,361 B2 | 2/2014 | Borillo et al. |
| 8,647,367 B2 | 2/2014 | Kassab et al. |
| 8,663,268 B2 | 3/2014 | Quinn et al. |
| 8,663,273 B2 | 3/2014 | Khairkhahan et al. |
| 8,685,055 B2 | 4/2014 | VanTassel et al. |
| 8,715,302 B2 | 5/2014 | Ibrahim et al. |
| 8,715,318 B2 | 5/2014 | Miles et al. |
| 8,740,934 B2 | 7/2014 | McGuckin, Jr. |
| 8,764,793 B2 | 7/2014 | Lee |
| 8,784,469 B2 | 7/2014 | Kassab |

(56) References Cited

U.S. PATENT DOCUMENTS

| | | |
|---|---|---|
| 8,795,328 B2 | 8/2014 | Miles et al. |
| 8,801,746 B1 | 8/2014 | Kreidler et al. |
| 8,828,051 B2 | 9/2014 | Javois et al. |
| 8,834,519 B2 | 9/2014 | van der Burg et al. |
| 8,840,641 B2 | 9/2014 | Miles et al. |
| 8,845,711 B2 | 9/2014 | Miles et al. |
| 9,011,551 B2 | 4/2015 | Oral et al. |
| 9,034,006 B2 | 5/2015 | Quinn et al. |
| 9,089,313 B2 | 7/2015 | Roue et al. |
| 9,131,849 B2 | 9/2015 | Khairkhahan et al. |
| 9,132,000 B2 | 9/2015 | VanTassel et al. |
| 9,161,830 B2 | 10/2015 | Borillo et al. |
| 9,168,043 B2 | 10/2015 | Van Der et al. |
| 9,186,152 B2 | 11/2015 | Campbell et al. |
| 9,351,716 B2 | 5/2016 | Miles et al. |
| 9,421,004 B2 | 8/2016 | Roue et al. |
| 9,445,895 B2 | 9/2016 | Kreidler |
| 9,474,516 B2 | 10/2016 | Clark et al. |
| 9,554,804 B2 | 1/2017 | Erzberger et al. |
| 9,592,058 B2 | 3/2017 | Erzberger et al. |
| 9,592,110 B1 | 3/2017 | Dan et al. |
| 9,649,115 B2 | 5/2017 | Edmiston et al. |
| 9,693,780 B2 | 7/2017 | Miles et al. |
| 9,693,781 B2 | 7/2017 | Miles et al. |
| 9,700,323 B2 | 7/2017 | Clark |
| 9,730,701 B2 | 8/2017 | Tischler et al. |
| 9,743,932 B2 | 8/2017 | Amplatz et al. |
| 9,763,666 B2 | 9/2017 | Wu et al. |
| 9,808,253 B2 | 11/2017 | Li et al. |
| 9,839,431 B2 | 12/2017 | Meyer et al. |
| 9,849,011 B2 | 12/2017 | Zimmerman et al. |
| 9,861,370 B2 | 1/2018 | Clark et al. |
| 9,883,864 B2 | 2/2018 | Miles et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 2002/0022860 A1 | 2/2002 | Borillo et al. |
| 2002/0049457 A1 | 4/2002 | Kaplan et al. |
| 2002/0095205 A1 | 7/2002 | Edwin et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111647 A1 | 8/2002 | Khairkhahan et al. |
| 2002/0169377 A1 | 11/2002 | Khairkhahan et al. |
| 2003/0023266 A1 | 1/2003 | Borillo et al. |
| 2003/0051735 A1 | 3/2003 | Pavcnik |
| 2003/0120337 A1 | 6/2003 | Van Tassel et al. |
| 2003/0191526 A1 | 10/2003 | Van Tassel et al. |
| 2003/0199923 A1 | 10/2003 | Khairkhahan et al. |
| 2003/0204203 A1 | 10/2003 | Khairkhahan et al. |
| 2003/0220667 A1 | 11/2003 | van der Burg et al. |
| 2004/0049210 A1 | 3/2004 | VanTassel et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0215230 A1 | 10/2004 | Frazier et al. |
| 2004/0220610 A1 | 11/2004 | Kreidler et al. |
| 2004/0225212 A1 | 11/2004 | Okerlund et al. |
| 2004/0230222 A1 | 11/2004 | van der Burg et al. |
| 2005/0004652 A1 | 1/2005 | van der Burg et al. |
| 2005/0033287 A1 | 2/2005 | Sra |
| 2005/0038470 A1 | 2/2005 | van der Burg et al. |
| 2005/0049573 A1 | 3/2005 | VanTassel et al. |
| 2005/0070952 A1 | 3/2005 | Devellian |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0177182 A1 | 8/2005 | van der Burg et al. |
| 2005/0234540 A1 | 10/2005 | Peavey et al. |
| 2005/0234543 A1 | 10/2005 | Glaser et al. |
| 2005/0267528 A1 | 12/2005 | Ginn |
| 2006/0009715 A1 | 1/2006 | Khairkhahan et al. |
| 2006/0116709 A1 | 6/2006 | Sepetka |
| 2007/0005147 A1 | 1/2007 | Levine |
| 2007/0083230 A1 | 4/2007 | Javois |
| 2007/0129753 A1 | 6/2007 | Quinn et al. |
| 2007/0135826 A1 | 6/2007 | Zaver et al. |
| 2007/0149988 A1 | 6/2007 | Michler et al. |
| 2007/0149995 A1 | 6/2007 | Quinn et al. |
| 2007/0179345 A1 | 8/2007 | Santilli |
| 2007/0270891 A1 | 11/2007 | McGuckin, Jr. |
| 2008/0033241 A1 | 2/2008 | Peh et al. |
| 2008/0125795 A1 | 5/2008 | Kaplan et al. |
| 2008/0243183 A1 | 10/2008 | Miller et al. |
| 2008/0294175 A1 | 11/2008 | Bardsley et al. |
| 2008/0312664 A1 | 12/2008 | Bardsley et al. |
| 2009/0005760 A1 | 1/2009 | Cartledge |
| 2009/0099596 A1 | 4/2009 | McGunkin, Jr. et al. |
| 2009/0112249 A1 | 4/2009 | Miles et al. |
| 2009/0143791 A1 | 6/2009 | Miller et al. |
| 2009/0157118 A1 | 6/2009 | Miller et al. |
| 2009/0264920 A1 | 10/2009 | Berenstein |
| 2009/0287145 A1 | 11/2009 | Cragg et al. |
| 2009/0306685 A1 | 12/2009 | Fill |
| 2009/0326577 A1 | 12/2009 | Johnson et al. |
| 2010/0076463 A1 | 3/2010 | Mavani et al. |
| 2010/0191279 A1 | 7/2010 | Kassab et al. |
| 2010/0228184 A1 | 9/2010 | Mavani et al. |
| 2010/0228279 A1 | 9/2010 | Miles et al. |
| 2010/0228285 A1 | 9/2010 | Miles et al. |
| 2010/0286718 A1 | 11/2010 | Kassab et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0009853 A1 | 1/2011 | Bertolero et al. |
| 2011/0022079 A1 | 1/2011 | Miles et al. |
| 2011/0022168 A1 | 1/2011 | Cartledge |
| 2011/0054515 A1 | 3/2011 | Bridgemann et al. |
| 2011/0082495 A1 | 4/2011 | Ruiz |
| 2011/0087271 A1 | 4/2011 | Sargent et al. |
| 2011/0178539 A1 | 7/2011 | Holmes, Jr. et al. |
| 2011/0208233 A1 | 8/2011 | McGunkin, Jr. et al. |
| 2011/0218389 A1 | 9/2011 | Gobel |
| 2011/0218566 A1 | 9/2011 | van der Burg et al. |
| 2011/0220120 A1 | 9/2011 | Frigstad et al. |
| 2011/0257674 A1 | 10/2011 | Evert et al. |
| 2011/0264119 A1 | 10/2011 | Bayon et al. |
| 2011/0307003 A1 | 12/2011 | Chambers |
| 2012/0010644 A1 | 1/2012 | Sideris et al. |
| 2012/0029553 A1 | 2/2012 | Quinn et al. |
| 2012/0065662 A1 | 3/2012 | van der Burg et al. |
| 2012/0065667 A1 | 3/2012 | Javois et al. |
| 2012/0157916 A1 | 6/2012 | Quinn et al. |
| 2012/0158022 A1 | 6/2012 | Kaplan et al. |
| 2012/0172927 A1 | 7/2012 | Campbell et al. |
| 2012/0221042 A1 | 8/2012 | Schwartz et al. |
| 2012/0239077 A1 | 9/2012 | Zaver et al. |
| 2012/0283585 A1 | 11/2012 | Werneth et al. |
| 2012/0283773 A1 | 11/2012 | VanTassel et al. |
| 2012/0316584 A1 | 12/2012 | Miles et al. |
| 2012/0323262 A1 | 12/2012 | Ibrahim et al. |
| 2012/0323267 A1 | 12/2012 | Ren |
| 2012/0323270 A1 | 12/2012 | Lee |
| 2012/0330342 A1 | 12/2012 | Jones |
| 2013/0006343 A1 | 1/2013 | Kassab |
| 2013/0012982 A1 | 1/2013 | Khairkhahan et al. |
| 2013/0018413 A1 | 1/2013 | Oral et al. |
| 2013/0018414 A1 | 1/2013 | Widomski et al. |
| 2013/0083983 A1 | 4/2013 | Zhong et al. |
| 2013/0110154 A1 | 5/2013 | van der Burg et al. |
| 2013/0116724 A1 | 5/2013 | Clark et al. |
| 2013/0165965 A1 | 6/2013 | Carlson et al. |
| 2013/0178889 A1 | 7/2013 | Miles et al. |
| 2013/0237908 A1 | 9/2013 | Clark |
| 2014/0005714 A1 | 1/2014 | Quick et al. |
| 2014/0046360 A1 | 2/2014 | van der Burg et al. |
| 2014/0074151 A1 | 3/2014 | Tischler et al. |
| 2014/0128903 A1 | 5/2014 | Alferness |
| 2014/0257320 A1 | 9/2014 | Fitz |
| 2014/0277074 A1 | 9/2014 | Kaplan et al. |
| 2014/0336699 A1 | 11/2014 | van der Burg et al. |
| 2014/0371789 A1 | 12/2014 | Hariton et al. |
| 2015/0005810 A1 | 1/2015 | Center et al. |

(56) References Cited

U.S. PATENT DOCUMENTS

| | | |
|---|---|---|
| 2015/0039021 A1 | 2/2015 | Khairkhahan et al. |
| 2015/0133989 A1 | 5/2015 | Lubock et al. |
| 2015/0196305 A1 | 7/2015 | Meyer et al. |
| 2016/0058539 A1 | 1/2016 | Vantassel et al. |
| 2016/0089151 A1 | 3/2016 | Siegel et al. |
| 2016/0106437 A1 | 4/2016 | van der Burg et al. |
| 2017/0042549 A1 | 2/2017 | Kaplan et al. |
| 2017/0042550 A1 | 2/2017 | Chakraborty et al. |
| 2017/0095238 A1 | 4/2017 | Rudman et al. |
| 2017/0100112 A1 | 4/2017 | Van Der et al. |
| 2017/0135801 A1 | 5/2017 | Delaney, Jr. et al. |
| 2017/0224354 A1 | 8/2017 | Tischler et al. |
| 2017/0281192 A1 | 10/2017 | Tieu et al. |
| 2017/0290594 A1 | 10/2017 | Chakraborty et al. |
| 2017/0340336 A1 | 11/2017 | Osypka |
| 2018/0185130 A1 | 7/2018 | Janardhan et al. |
| 2018/0206830 A1 | 7/2018 | Khairkhahan et al. |
| 2018/0250014 A1 | 9/2018 | Melanson et al. |
| 2018/0338824 A1 | 11/2018 | VanTassel et al. |
| 2019/0083075 A1 | 3/2019 | Onushko et al. |
| 2019/0125362 A1 | 5/2019 | Tischler |
| 2019/0336137 A1 | 11/2019 | Chakraborty et al. |

FOREIGN PATENT DOCUMENTS

| | | |
|---|---|---|
| DE | 102006056283 | 6/2008 |
| EP | 1223890 B1 | 4/2004 |
| EP | 1227770 B1 | 9/2004 |
| EP | 1225843 B1 | 2/2005 |
| EP | 1469790 B1 | 10/2016 |
| EP | 3085310 A1 | 10/2016 |
| EP | 2872051 B1 | 3/2017 |
| JP | 2003-512128 | 4/2003 |
| JP | 2003-529384 | 10/2003 |
| JP | 2012-530551 | 12/2012 |
| WO | WO 00/27292 | 5/2000 |
| WO | WO2009009466 | 1/2009 |
| WO | WO2014/011865 | 1/2014 |
| WO | WO 2014/164572 | 10/2014 |
| WO | WO2016/033170 | 3/2016 |
| WO | WO 2017/161283 | 9/2017 |
| WO | WO2018/185255 | 10/2018 |
| WO | WO2018/185256 | 10/2018 |

OTHER PUBLICATIONS

Extended European Search Report in European Patent Case No. EP 14 77 9640 dated Sep. 30, 2016.

International Search Report and Written Opinion dated Jan. 19, 2017, in International Application No. PCT/US2016/056450.

International Search Report and Written Opinion dated Jul. 3, 2014, in International Application No. PCT/US2014/022865.

International Search Report dated Jul. 10, 2019, in International Application No. PCT/US2019/29364.

International Search Report issued in International Patent Application No. PCT/US2020/016854, dated Jun. 8, 2020.

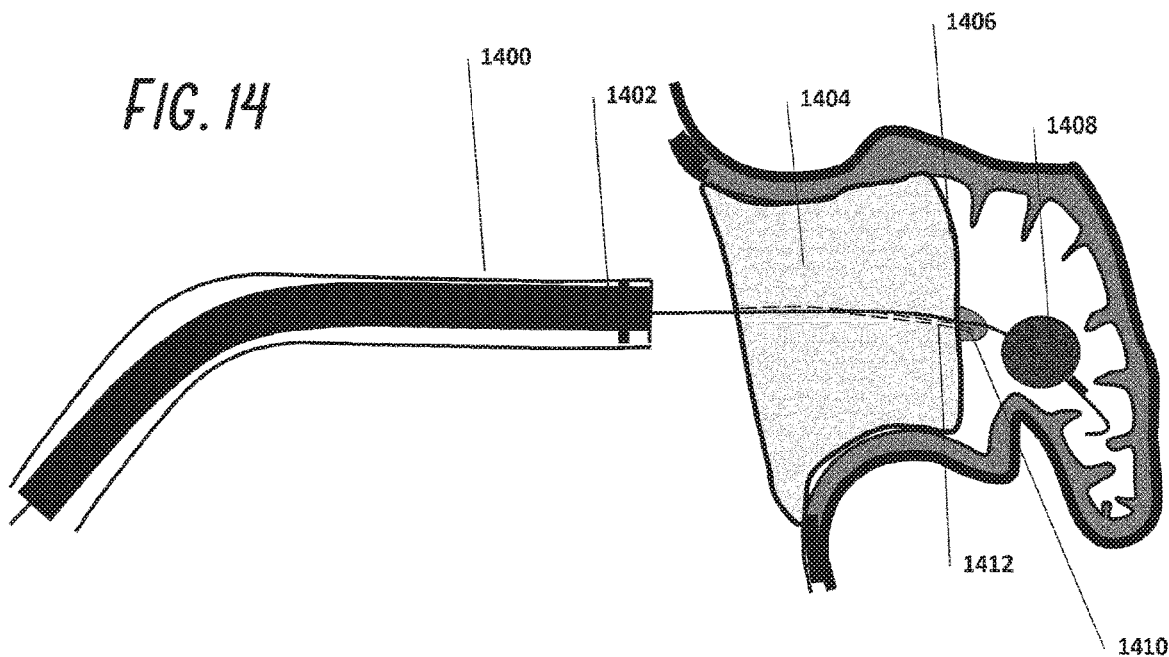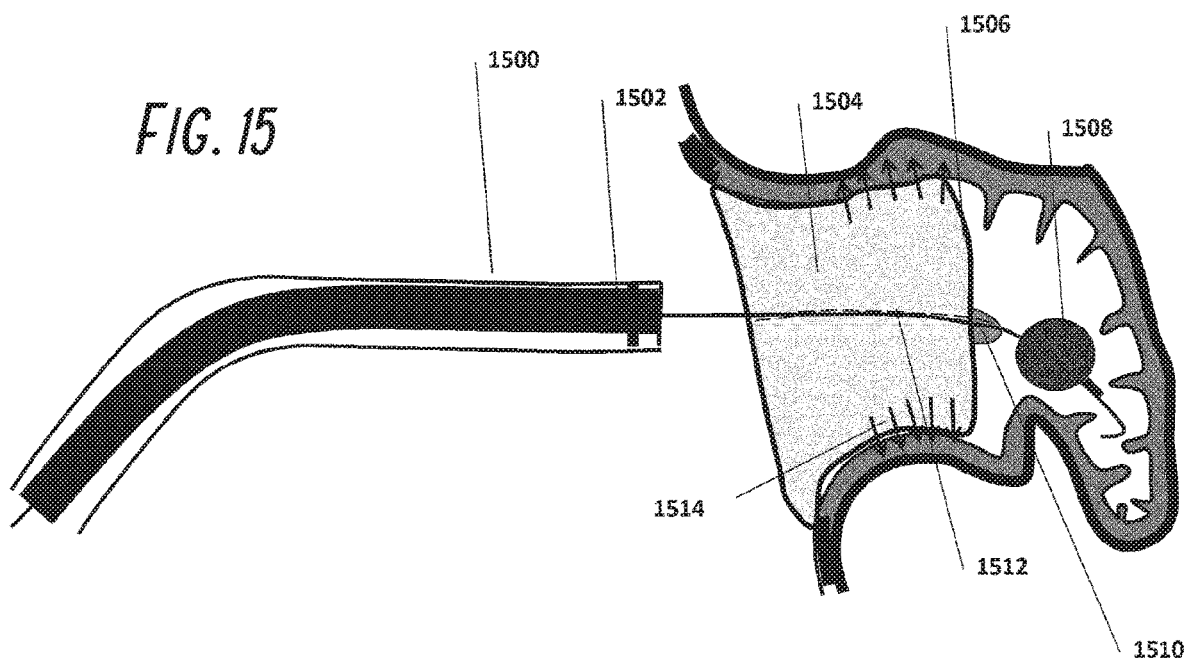

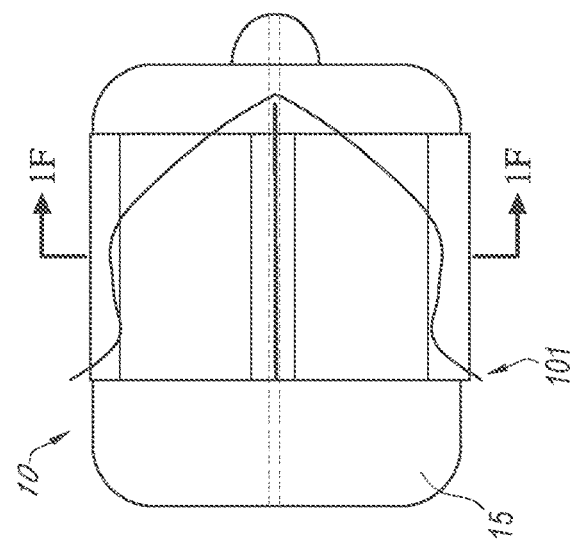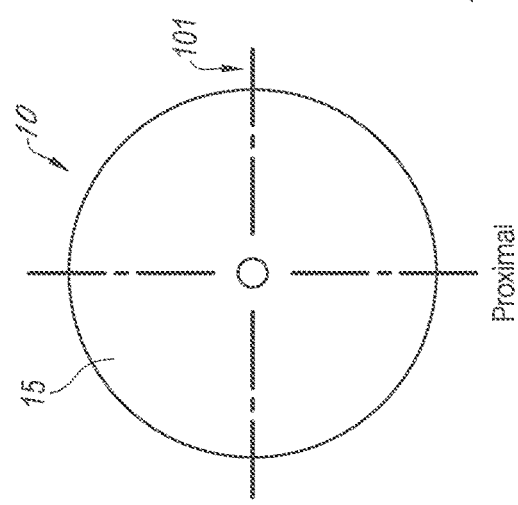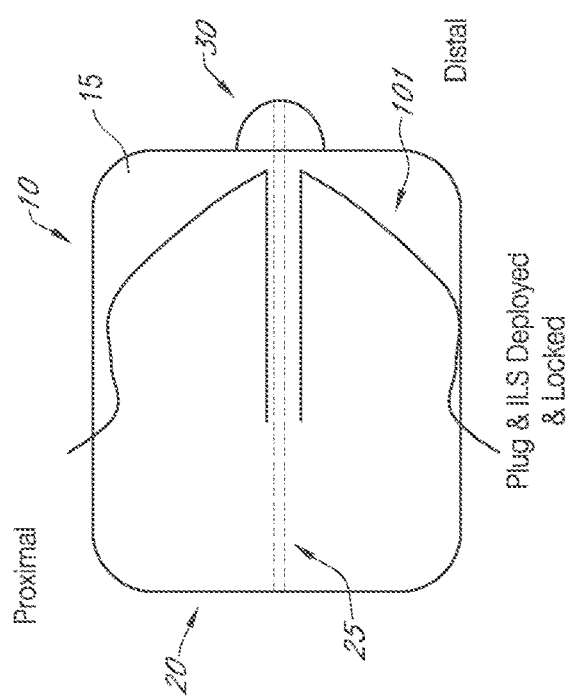

Plug Deployed

Plug with ILS Loaded

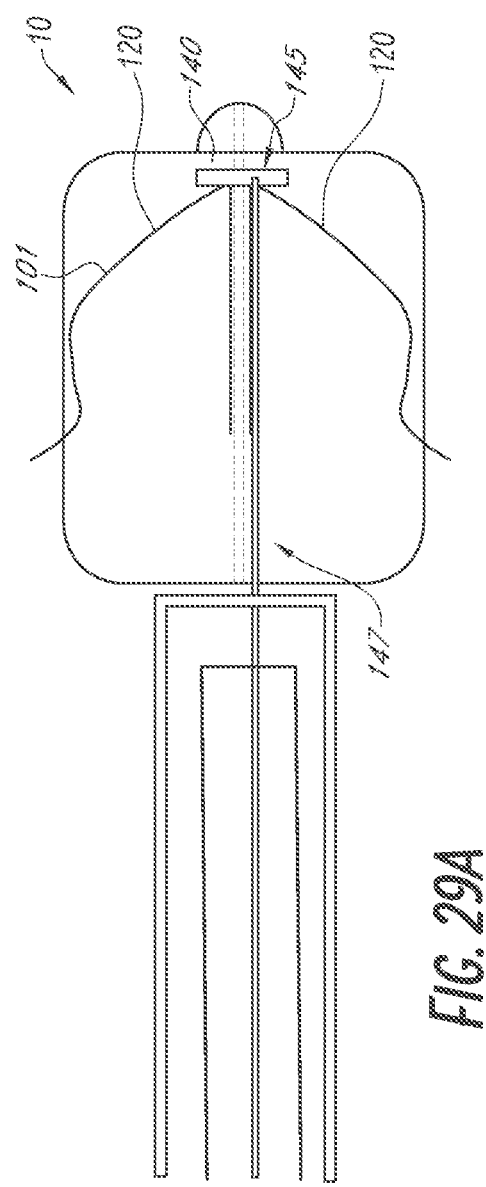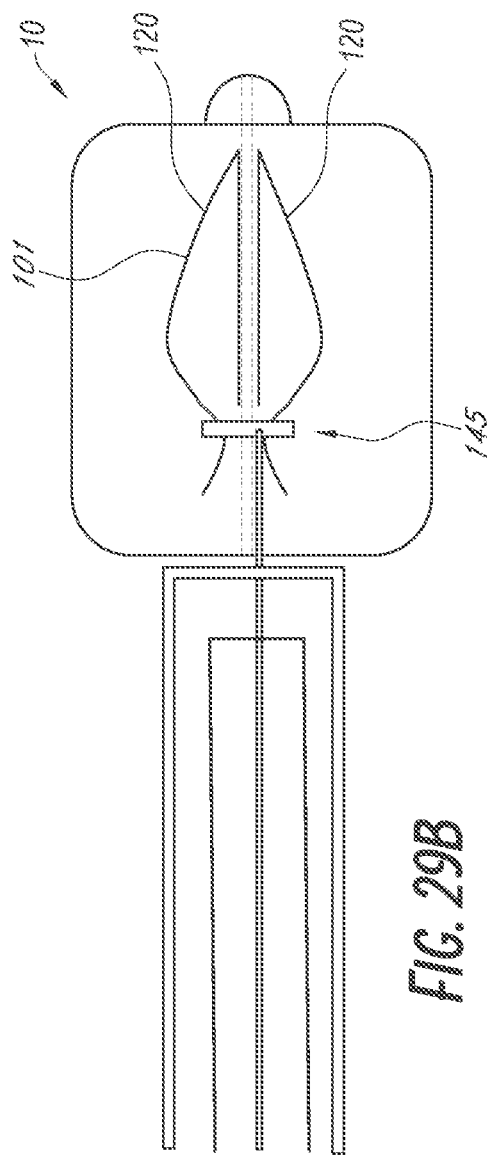
FIG. 29A
FIG. 29B

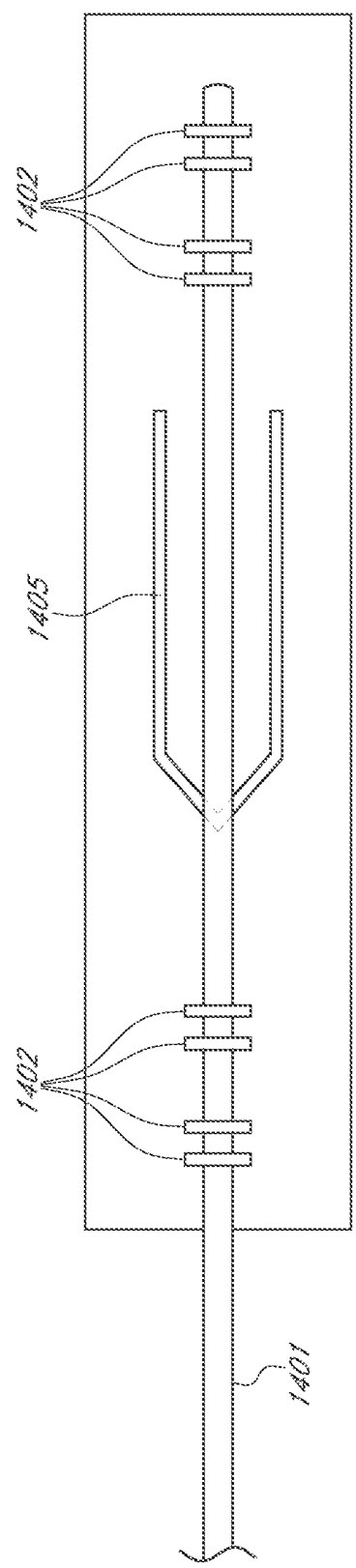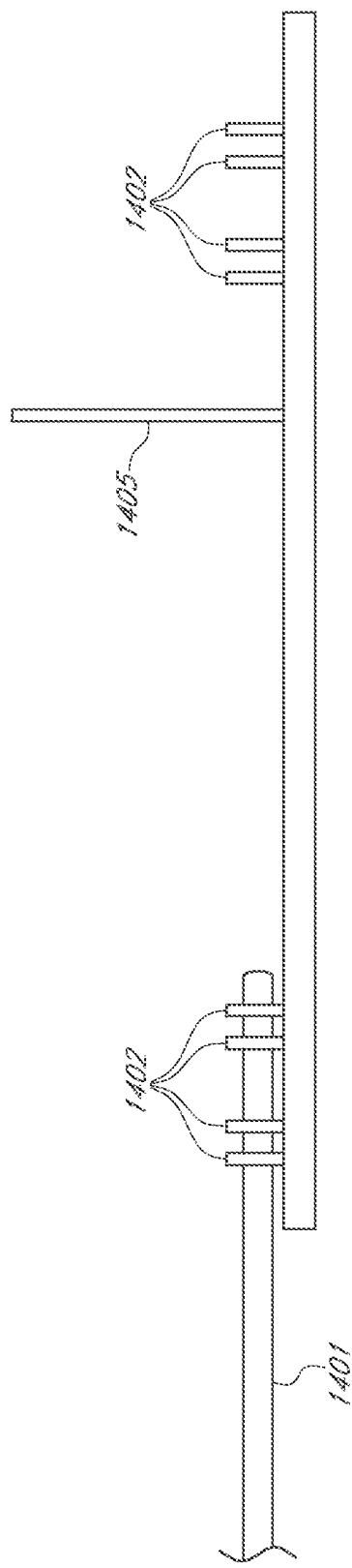
FIG. 40A
FIG. 40B

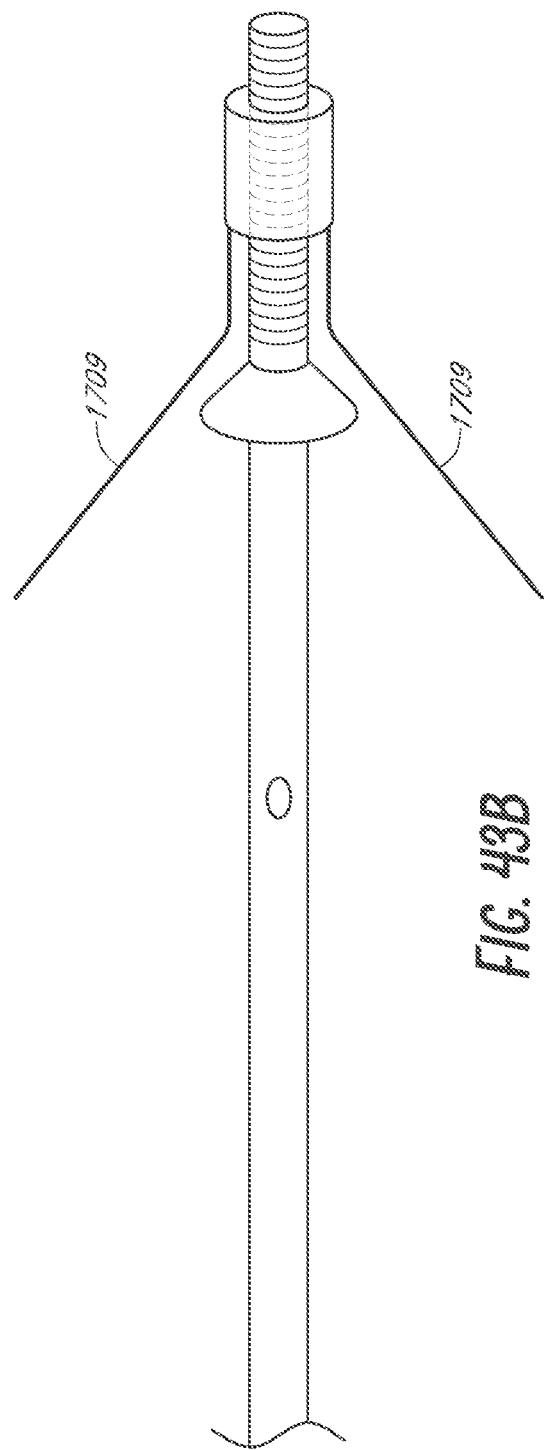

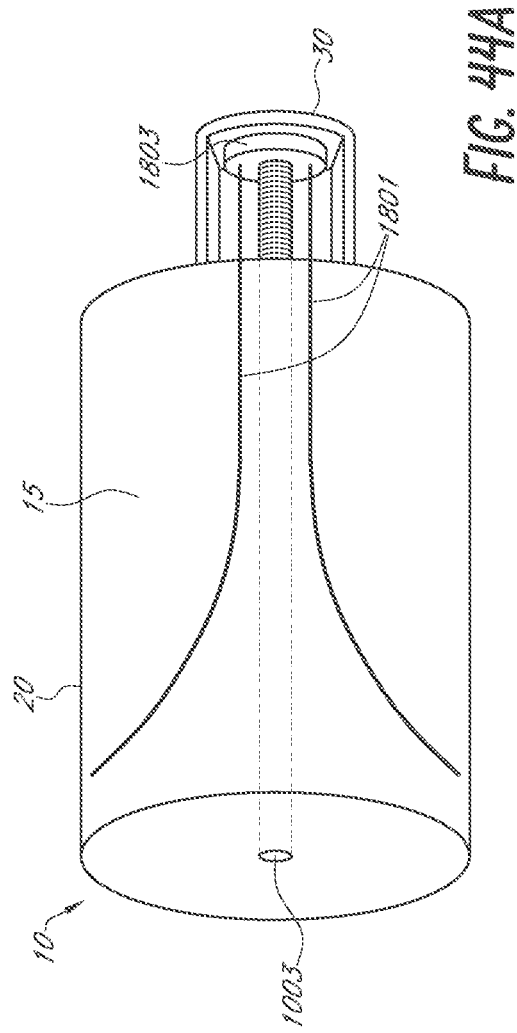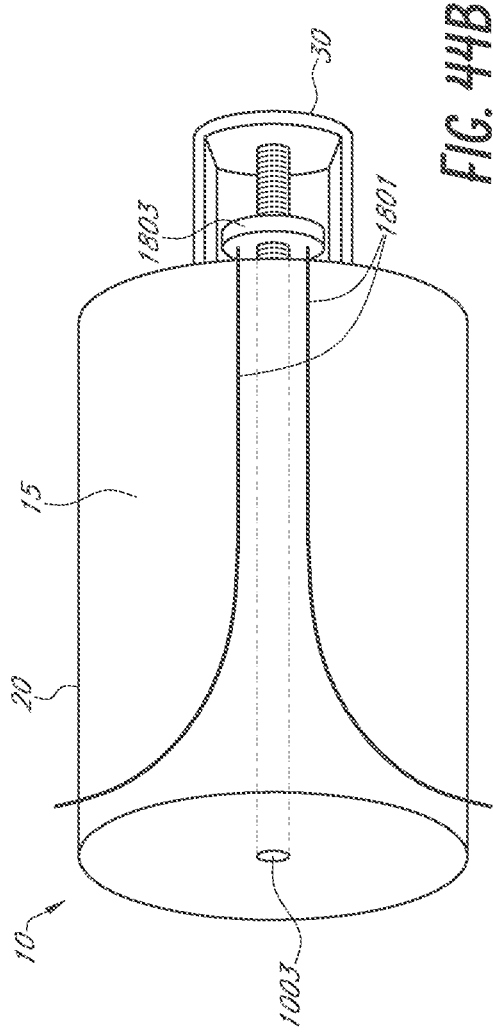

DEVICES AND METHODS FOR EXCLUDING THE LEFT ATRIAL APPENDAGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. For example, this application is a continuation of U.S. application Ser. No. 15/290,692 entitled "DEVICES AND METHODS FOR EXCLUDING THE LEFT ATRIAL APPENDAGE" and filed on Oct. 11, 2016, which is a continuation in part of U.S. application Ser. No. 14/203,187 entitled "DEVICES AND METHODS FOR EXCLUDING THE LEFT ATRIAL APPENDAGE" and filed on Mar. 10, 2014, and claims the benefit of priority under 35 U.S.C. § 119(e) of U.S. Provisional Application No. 62/240,124 entitled "DEVICES AND METHODS FOR EXCLUDING THE LEFT ATRIAL APPENDAGE" and filed on Oct. 12, 2015, the entire disclosure of each of which is incorporated herein by reference for all purposes and forms a part of this specification.

BACKGROUND

Field

This development relates generally to systems, devices and methods for excluding the left atrial appendage (LAA). In particular, systems, devices and methods for excluding the LAA using an expandable foam implant with deployable anchors are described herein.

Description of the Related Art

Atrial fibrillation (Afib) is a condition in which the normal beating of the left atrium (LA) is chaotic and ineffective. The left atrial appendage (LAA) is a blind pouch off the LA. In patients with Afib blood stagnates in the LAA facilitating clot formation. These clots (or clot fragments) have a tendency to embolize or leave the LAA and enter the systemic circulation. A stroke occurs when a clot/clot fragment embolizes and occludes one of the arteries perfusing the brain. Anticoagulants, e.g. Coumadin, have been shown to significantly reduce the stroke risk in Afib patients. These drugs reduce clot formation but also increased bleeding complications including hemorrhagic strokes, subdural hematoma, and bleeding in the gastrointestinal tract.

There are about 8 million people in the US and EU with Afib. About 4.6 million of these patients are at a high risk for stroke and would benefit from anticoagulation. A large portion of these patients cannot take anticoagulants due to an increased bleeding risk, leaving their stroke risk unaddressed. The prevalence of Afib increases with age.

Several devices for occluding the LAA are described in the prior art and each has limitations this invention improves upon. The prior art devices are metal structures which are circular in cross section and are made to expand to fill the LAA ostium. These devices are offered in many sizes and must be closely matched to the highly variable LAA anatomy. This is difficult to do using fluoroscopy and often requires adjunctive imaging in the form of transesophageal echocardiography (TEE), cardiac CT and MRI, all with three dimensional reconstructions. If the device is significantly oversized, the LAA ostium may become overstretched leading to tearing, resulting in bleeding into the pericardial space. If the device is too small, it will not adequately seal the ostium and may be prone to embolization. Even if sized correctly, the device forces the oval LAA ostium to take the round shape of the device, often resulting in residual leakage at the edges due to poor sealing.

Anchoring of these implants in the proper location is described in the prior art devices predominately using an array of radially disposed barbs or hooks that engage into the surrounding cardiac tissue upon expansion of the device. The device must therefore have sufficient spring force or stiffness for the barbs to engage the surrounding tissue. These barbs may lead to leaking of blood through the tissue into the pericardial space which may lead to cardiac tamponade. Furthermore, the geometry of these barbs and hooks prevent repositioning once the implant is fully expanded.

For all of these reasons it would be desirable to have a device which conforms to the oval shape of the LAA, does not require an excessive number of sizes therefore negating the need for extensive pre-procedure imaging, can be easily repositioned after it is fully expanded, then secured in place once the final position has been optimized.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

Devices and methods are described for occluding the left atrial appendage (LAA) to exclude the LAA from blood flow to prevent blood from clotting within the LAA and subsequently embolizing, particularly in patients with atrial fibrillation. A foam implant is delivered via transcatheter delivery into the LAA and anchored using an internal locking system of the implant. The locking system includes deployable anchors that can be deployed after deployment of the foam implant from the delivery catheter and expansion of the foam within the LAA. The implant location can thus be verified before deploying the anchors to secure the implant. The locking system can be reversible to allow retraction of the anchors and repositioning or retrieval of the implant.

The devices and methods allow for occluding the LAA with a foam plug to prevent blood from clotting within the LAA and subsequently embolizing. An implantable device is delivered through a catheter that is tracked over a guide wire through the vascular system. The guide wire lumen within the foam is expandable, to allow for placement of the guide wire, then is self-closing upon removal of the guide wire. Foams, which can be tubular in shape with a central lumen, are described that are collapsed for delivery and then expand in place within the LAA. The plug is anchored by tissue ingrowth from the left atrium (LA) and LAA into the foam, by independent and/or integrated repositionable anchors, barbs, and/or by distal anchoring elements. For example, independent repositionable anchors are described which deploy through openings in the compressible foam plug and tubular film and can be expanded, re-collapsed, and locked through the central guide wire lumen. Repositionable atraumatic anchor system embodiments are also disclosed which can be independent structures or integral to the foam plug and/or skin. Foam plugs are described that are encapsulated with jackets or skins that can be tubular in shape that are sufficiently strong to enable handling of the plugs without tearing, allow for repositioning and retrieval of the plugs, provide a thromboresistant surface within the LA which will encourage formation of a neointima, assist in the creation of occlusion zones designed to encourage thromboresistance and endothelialization from the blood and adjacent tissue and anchoring zones designed to promote fast and tenacious tissue ingrowth into the compressible implant from the adjacent non-blood tissue, and can assist in closure at the ostium. These jackets or skins can be independent or can be attached to the foam plugs. Retrieval finials can be attached at one or more points to aid in retrieval of an embolized device and to increase radiopacity.

In one aspect, a left atrial appendage occlusion device is described. The device includes an open cell foam body and an internal locking system. The body has a proximal end, a distal end and an outer skin. The proximal end is configured to face a left atrium and the distal end is configured to face the left atrial appendage following implantation in the left atrial appendage. The body can be compressed for delivery within a delivery catheter and can self-expand when removed from the delivery catheter. The internal locking system is coupled with the body and comprises at least one deployable tissue anchor. The deployable anchor is configured to deploy from a constrained configuration within the body to a deployed configuration where a tissue engaging segment of the anchor extends outside the body to secure the body within the left atrial appendage. The deployable anchor is configured to deploy to the deployed configuration after the body expands within the left atrial appendage. The deployable anchor is retractable from the deployed configuration to a retracted configuration within the body.

In some embodiments, the internal locking system further comprises a plurality of the deployable anchors rotatably coupled with the body, wherein the plurality of anchors are configured to rotate to the deployed and retracted configurations. The internal locking system may comprise four of the deployable anchors. In some embodiments, the body further comprises a plurality of axially extending slots corresponding to the plurality of anchors, wherein each of the plurality of anchors is configured to deploy and retract through the corresponding axial slot.

In some embodiments, the internal locking system further comprises a restraint that restrains the anchor in the constrained configuration, and the anchor is deployed from the constrained configuration to the deployed configuration by removing the restraint from the anchor. The restraint may be a sheath that restrains the anchor in the constrained configuration by covering the anchor, wherein the anchor is deployed from the constrained configuration to the deployed configuration by removing the sheath from covering the anchor. The restraint may be a lasso that restrains the anchor in the constrained configuration by surrounding the anchor, and the anchor is deployed from the constrained configuration to the deployed configuration by removing the lasso from surrounding the anchor.

In some embodiments, the internal locking system further comprises a moveable mount coupled with an end of the anchor, and the anchor is deployed from the constrained configuration to the deployed configuration by axially moving the mount.

In some embodiments, the internal locking system further comprises a constraint configured to move over the anchor to cause the anchor to retract. The constraint may be a ring configured to slide over the anchor to cause the anchor to retract.

In some embodiments, the skin comprises ePTFE.

In some embodiments, the device further comprises at least one tissue ingrowth surface on a sidewall of the body.

In some embodiments, the device further comprises a plurality of openings in the skin to permit tissue ingrowth into the open cell foam body. The plurality of openings of the skin may be located in an anchoring region of the device located at least between the proximal and distal ends of the device, and the device may further comprise an occlusion region located at the proximal end of the device and configured to encourage thromboresistance and endothelialization from the blood and adjacent tissue.

In another aspect, a left atrial appendage closure system is described. The system comprises a delivery catheter and a left atrial appendage occlusion device. The delivery catheter comprises an elongate flexible tubular body, having a proximal end and a distal end and at least one lumen extending therethrough. The left atrial appendage occlusion device is configured to be compressed within the delivery catheter and to self-expand upon deployment from the delivery catheter. The device comprises a self-expandable open cell foam body coupled with an internal locking system. The internal locking system comprises a deployable anchor configured to deploy from a constrained configuration to a deployed configuration after the body expands within the left atrial appendage and is configured to retract from the deployed configuration to a retracted position within the body.

In some embodiments, the system further comprises an axially movable deployment control extending through a lumen of the body, for deploying the deployable anchor. The system may further comprise an axially movable deployment control extending through a lumen of the body, for deploying the foam body from the distal end of the closure system. The internal locking system may further comprise a restraint that restrains the anchor in the constrained configuration, and the anchor is actively deployed from the constrained configuration to the deployed configuration by removing the restraint from the anchor using an axially movable deployment control extending through a lumen of the body. The internal locking system may further comprise a moveable mount coupled with an end of the anchor, and the anchor is actively deployed from the constrained configuration to the deployed configuration by axially moving the mount using an axially movable deployment control extending through a lumen of the body.

In another aspect, a method of excluding a left atrial appendage is described. The method comprises advancing a guidewire into the left atrial appendage, advancing a distal end of a delivery catheter over the guidewire and into the left atrial appendage, and deploying a left atrial appendage occlusion device from the distal end of the delivery catheter. The device comprises an expandable foam body coupled with an internal locking system having a deployable anchor, and the body expands within the left atrial appendage upon deploying from the distal end of the delivery catheter. The method further comprises actively deploying the deployable anchor after the body expands within the left atrial appendage. The deployable anchor is configured to retract from the deployed configuration to a retracted position within the body. In some embodiments, the method further comprises retracting the deployable anchor from the deployed configuration to the retracted position.

In another aspect, a left atrial appendage occlusion device is described. The device comprises an expandable foam body and an internal locking system. The body can be compressed for delivery within a delivery catheter and can self-expand when removed from the delivery catheter. The internal locking system is coupled with the body and comprises a deployable anchor configured to deploy from a constrained configuration within the body to a deployed configuration where the anchor extends outside the body to secure the body within the left atrial appendage. The body is configured to expand upon removal from the delivery catheter, and the deployable anchor is configured to deploy to the deployed configuration after the body expands.

In another aspect, a left atrial appendage occlusion device is described. The device comprises an expandable foam body and an internal locking system. The body can be compressed for delivery within a delivery catheter and can self-expand when removed from the delivery catheter. The internal locking system is coupled with the body and comprises a deployable anchor configured to deploy from a constrained configuration within the body to a deployed configuration where the anchor extends outside the body to secure the body within the left atrial appendage. The deployable anchor is configured to retract from the deployed configuration to a retracted configuration within the body such that the body can be repositioned within the left atrial appendage.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIG. 14 is an illustration as in FIG. 13, with the occlusion device fully deployed within the left atrial appendage.

FIG. 15 is an illustration as in FIG. 14, showing the deployment of adhesives or other anchoring structures to retain the occlusion device within the left atrial appendage.

FIGS. 27A-27G are various views of an embodiment of a device for occlusion of the left atrial appendage (LAA) with an internal locking system for securing the device.

FIGS. 29A-29B are sequential side views of an unlocking mechanism that may be used with the various devices and plugs described herein for occlusion of the LAA, such as the device of FIGS. 27A-27G.

FIGS. 40A-40B are perspective views of an embodiment of a deployable anchor activated by a lock wire and shown, respectively, in the constrained and deployed configuration, that may be used with the various devices for occlusion of the LAA described herein.

FIGS. 43A-43C are sequential side views of an embodiment of a device for occlusion of the LAA shown, respectively, constrained by a lasso, deployed, and adjusted with a mount.

FIGS. 44A-44C are side views of an embodiment of a device for occlusion of the LAA having an adjustable two stage anchor system activated by moving a mounting base along a rod.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

The devices and related methods are described herein in connection with use in occluding, i.e. excluding, a left atrial appendage (LAA). The various figures show various embodiments of LAA occlusion devices, systems and methods for delivery of the LAA occlusion devices, and/or methods of using the device to occlude a LAA. The various systems, devices and methods described herein may include the same features and/or functionalities as other LAA occlusion systems, devices and methods as described, for example, in U.S. application Ser. No. 14/203,187 entitled "DEVICES AND METHODS FOR EXCLUDING THE LEFT ATRIAL APPENDAGE" and filed on Mar. 10, 2014, and/or as described in U.S. Provisional Application No. 62/240,124 entitled "DEVICES AND METHODS FOR EXCLUDING THE LEFT ATRIAL APPENDAGE" and filed on Oct. 12, 2015, the entire disclosure of each of which is incorporated herein by reference for all purposes and forms a part of this specification.

Figure 1:
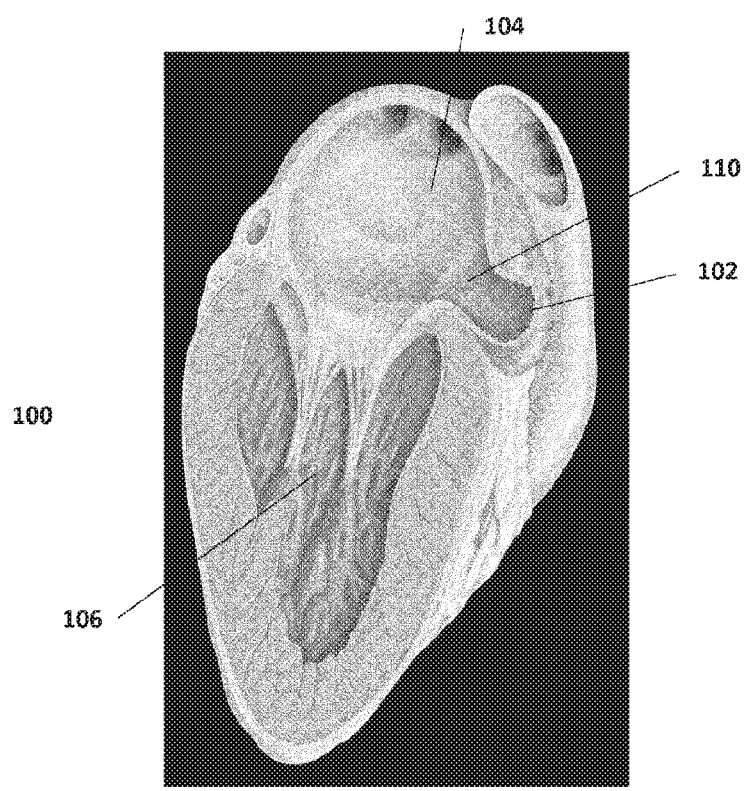
FIG. 1 shows the anatomy of the left atrium and left atrial appendage.

The heart 100 is shown in FIG. 1 with the left atrial appendage (LAA) 102 which is a cavity emanating from the left atrium (LA) 104. The LAA 102 is quite variable in shape in all dimensions. If the heart is not beating normally, a condition called atrial fibrillation, blood within the LAA becomes stagnant which promotes clot formation. If blood clots within the LAA, the clots may pass from the LAA 102 to the LA 104, to the left ventricle 106 and out of the heart 100 into the aorta. Vessels that bring blood to the brain branch off the aorta. If the clot passes to the brain via these vessels, it may get stuck and occlude a small vessel in the brain which then causes an ischemic stroke. Strokes have severe morbidities associated with them.

The opening of the LAA 102 to the LA 104 is called an ostium 110. The object of this invention is to occlude the ostium 110 thereby sealing off the LA 104 from the LAA 102. The ostium 110, is oval, highly variable and dependent of loading conditions, i.e., left atrial pressure.

Figure 2:
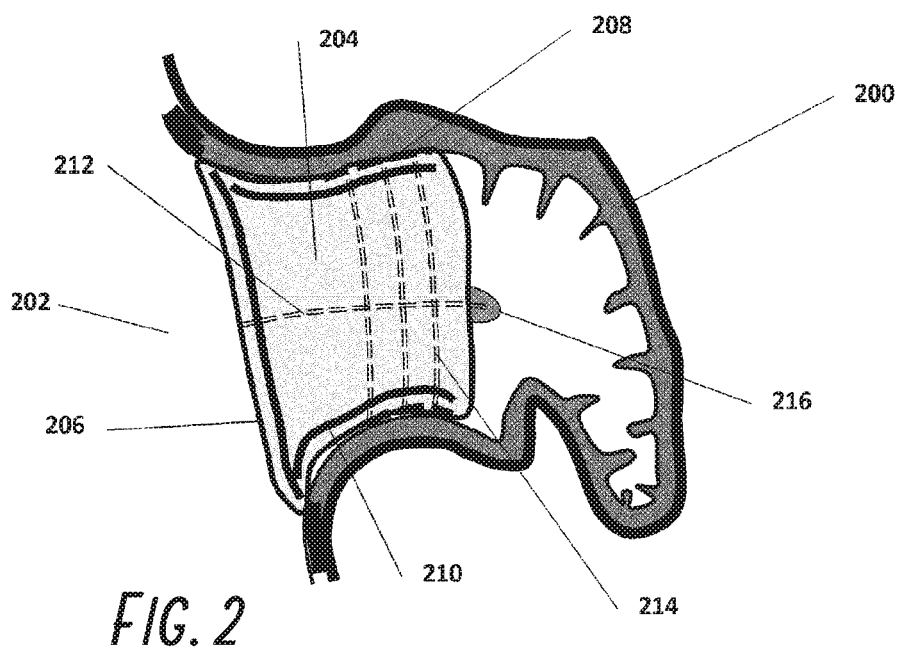
FIG. 2 shows a left atrial appendage with one foam plug embodiment in place that uses adhesive.

One embodiment of the LAA occlusion device is shown in FIG. 2. The occlusion device or plug 204 is placed within the LAA 200 at its opening to the LA 202. It is understood that the "plugs" described herein, such as the plug 204, may have the same or similar features as other implantable "devices" described herein, such as the device 10, and vice versa. The plug 204 comprises an expandable media such as an open cell foam which enables collapse and expansion of the plug and also to enhance ingrowth of tissue into the foam. The foam plug 204 is at least partially encapsulated within a thin strong layer 206 such as ePTFE (expanded polytetrafluoroethylene), polyolefin or polyester. The layer 206 may be referred to herein as a "skin." Alternatively bioabsorbable materials could be utilized such as PLA, PGA, PCL, PHA, or collagen. This thin encapsulating layer can be oriented or otherwise modified to be elastomeric in at least one direction, such as radially.

The plug may be made of polyurethane, polyolefin, PVA, collagen foams or blends thereof. One suitable material is a polycarbonate-polyurethane urea foam with a pore size of 100-250 um and 90-95% void content. The foam could be non-degradable or use a degradable material such as PLA, PGA, PCL, PHA, and/or collagen. If degradable, the tissue from the LAA will grow into the foam plug and replace the foam over time. The plug 204 may be cylindrical in shape in an unconstrained expansion but may also be conical with its distal end smaller than the proximal end or reversed. It could also be oval in cross section to better match the opening of the LAA.

The foam plug 204 is oversized radially in an unconstrained expansion to fit snuggly into the LAA and may be 5-50 mm in diameter depending on the diameter of the target LAA. The length "L" of the plug is similar to or greater than its diameter "D" such that the L/D ratio is about or greater than about 1.0 or greater than about 1.5 or greater than about 2.0 to maximize its stability. In some embodiments, the length may be less than the diameter such that the L/D ratio is less than 1.0. The compliance of the material is designed such that it pushes on the walls of the LAA with sufficient force to maintain the plug in place but without overly stretching the LAA wall. The foam and/or skin also conforms to the irregular surfaces of the LAA as it expands, to provide a complementary surface structure to the native LAA wall to further enhance anchoring and promote sealing. Thus, while some left atrial appendage occlusion devices in the prior art include a mechanical frame which forces at least some aspect of the left atrial appendage into a circular configuration, the expandable foam implant of the present invention conforms to the native configuration of the left atrial appendage. In one embodiment, the structure of the foam may be fabricated such that squeezing axially on the opposing ends of the foam causes the foam to increase in diameter.

Figure 3:
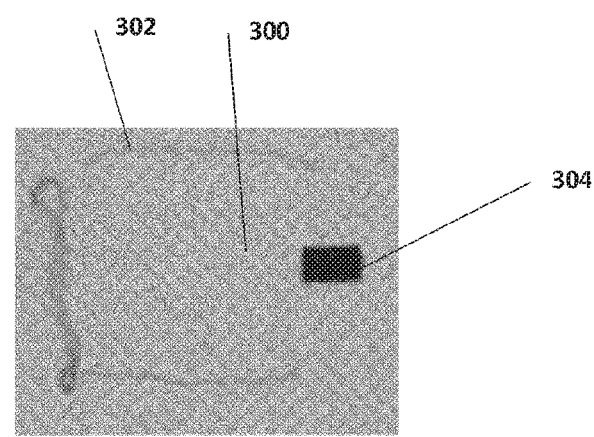
FIG. 3 shows an x-ray image of a foam plug.

The ePTFE or foam material may be provided with one or two or more radiopaque markers such as radiopaque threads 210 or be filled with or impregnated with a radiopaque filler such as barium sulfate, bismuth subcarbonate, or tungsten which permit the operator to see under x-ray the plug for proper positioning in the anatomy. An x-ray image is shown in FIG. 3 where one cannot see the foam plug 300 but can clearly see the threads 302 and the crimp 304 (discussed below). This thread or ribbon may be made from a radiopaque metallic wire such as platinum or tungsten or a polymer with a radiopaque filler such as barium, bismuth, tantalum, tungsten, titanium or platinum.

The outer ePTFE layer may be formed from a tube with a diameter about the same diameter of the foam plug and a wall thickness between about 0.0001" and about 0.001" thick and serves to allow one to collapse and pull on the plug without tearing the foam material. The ePTFE material also serves as the blood contacting surface facing the left atrium 206 and has pores or nodes such that blood components coagulate on the surface and an intimal or neointimal covering of tissue grows across it and anchors tightly to the material. Pore sizes within the range of from about 4µ to about 110µ, ideally 5-35µ are useful for formation and adherence of a neointima.

The outer covering 206 may be constructed of materials other than ePTFE such as woven fabrics, meshes or perforated films made of FEP, polypropylene, polyethylene, polyester or nylon. The covering should have a low compliance (non-elastic), at least longitudinally, be sufficiently strong as to permit removal of the plug, a low coefficient of friction, and be thromboresistant. The outer covering serves as a matrix to permit plug removal as most foams are not sufficiently strong to resist tearing when pulled. The plug can also be coated with or contain materials to enhance its ultrasonic echogenic profile, thromboresistance, lubricity, and/or to facilitate echocardiographic visualization, promote cellular ingrowth and coverage.

The outer covering has holes in it to permit contact of the LAA tissue with the foam plug to encourage ingrowth of tissue into the foam plug pores. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device. In one embodiment, holes are placed distally to enhance tissue ingrowth from the LAA wall.

Figure 20:
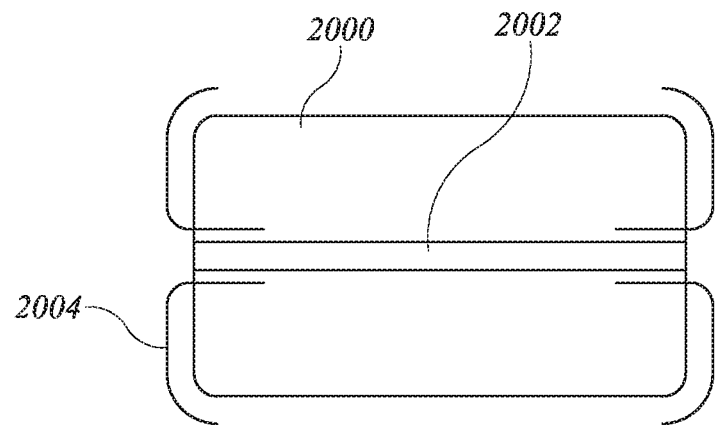
FIG. 20 shows a plug with proximal and distal caps.

In one implementation of the invention, the implant is provided with proximal and distal end caps of ePTFE, joined together by two or three or four or more axially extending strips of ePTFE. The axially extending strips are spaced apart from each other circumferentially, to provide at least two or three or four or more laterally facing windows through which the open cell foam body will be in direct contact with the tissue wall of the left atrial appendage. This outer covering could be a mesh or netting as well. As shown in FIG. 20, the covering 2004 is only on the proximal and distal faces of the plug 2000. They may be glued to the foam plug and then crimped to the center tube 2002.

Figure 21:
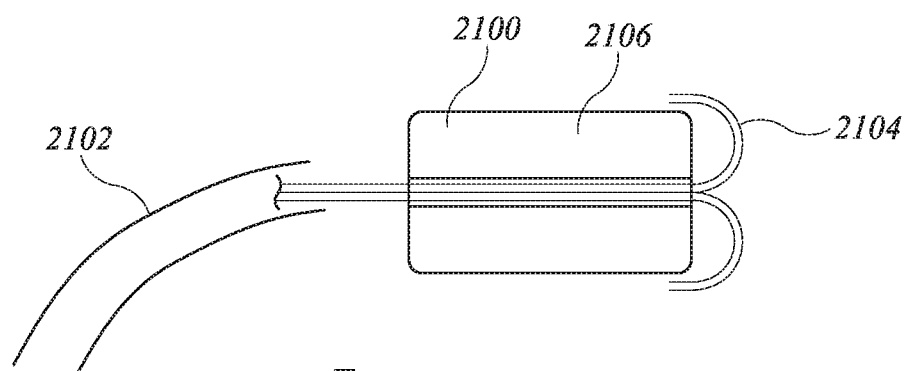
FIG. 21 shows a plug adhesive delivery system.

The implantable plug 204 or device 10 (as described below) may be anchored and secured in place in the LAA by tissue ingrowth and/or with additional anchoring features. In some embodiments, the plug or device 10 may be anchored by tissue ingrowth alone. In some embodiments, other anchoring means may be implemented. One means of adhering the foam plug in place within the LAA is to use an adhesive, such as a low viscosity cyanoacrylate (1-200 cps). The adhesive is injected into place along the sidewall near the distal end of the foam plug 208. Holes in the ePTFE covering permit the adhesive to interact between the foam plug 204 and the LAA wall 200. Injection of the adhesive may be accomplished with several means, one of which is to inject through the catheter into the center lumen 212. Passages 214 serve to guide the adhesive to the correct location. The distal end of the foam plug must be restricted at that time to prevent the adhesive from exiting the distal crimp 216. Alternatively, FIG. 21 shows tubes 2104 that are pre-placed through the guide catheter 2102, through the center lumen of the plug 2106 and bend backwards in the LAA to the distal end of the plug 2100. These tubes 2104 pass all the way to the proximal end of the guide catheter 2102 where a fitting is attached to permit injection of the adhesive which then exits the small tubes 2104 at the desired location of the plug. These tubes are made of polyethylene, polypropylene or FEP so that the adhesive will not adhere to the tubes. The tubes 2104 are withdrawn after injection through the guide catheter out of the patient.

Other one part adhesives including aqueous cross linking adhesives, polyurethane, PEG, PGA, PLA, polycaprolactone or a lycine-derived urethane may be used. In addition, these adhesives may be made in two components such that one component is adherent to the foam and the second injected in vivo. Also, these two component adhesives may be injected simultaneously to mix in vivo to prevent fouling of injection tubes.

Figure 4:
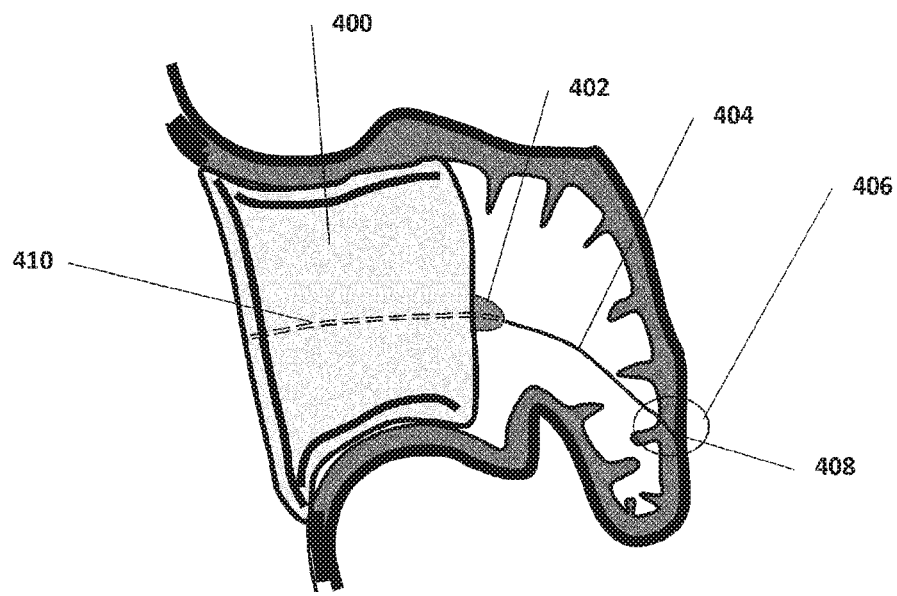
FIG. 4 shows a left atrial appendage with foam embodiment and distal anchor in place.
Figure 5:
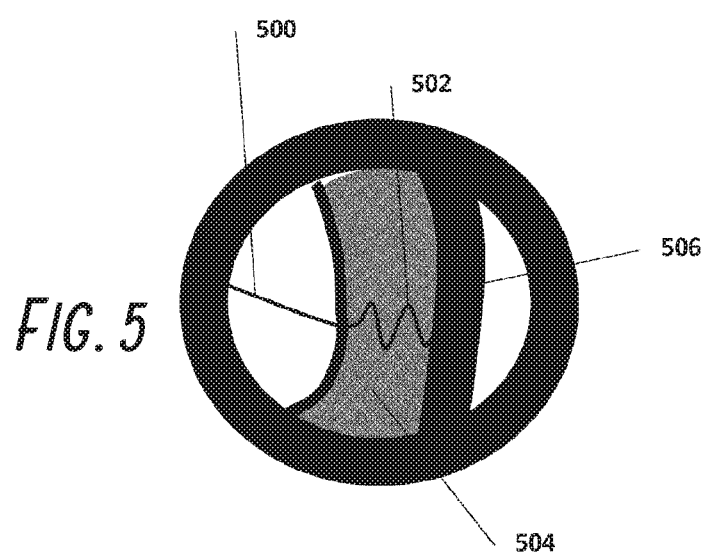
FIG. 5 shows a screw anchor.

An alternative anchoring means for plug 400 is one or two or more distal anchors as shown in FIG. 4. Wire 404 is passed through the center lumen 410 into the LAA and attached to the distal wall of the LAA. In this case, a screw wire 408 is threaded into the wall of the LAA 406. A closer detail of this is seen in FIG. 5 as screw 502 is shown embedded into the LAA wall 504 but not all the way through the epicardial surface 506.

Additional means of anchoring include the use of a plurality of hooks or barbs or graspers to grab the distal wall and baskets, malecots, distal foam plugs and Nitinol wire birds nests that open within the LAA and push outward on the wall or engage the protrusions of the LAA. It may be desirable to place the plug then engage the anchor as a secondary step. One such embodiment could include a multitude of nitinol wires with a ball or catch welded proximal to the anchor tip. These could be gathered with the delivery catheter then released when the ideal plug position has been confirmed.

Figure 6:
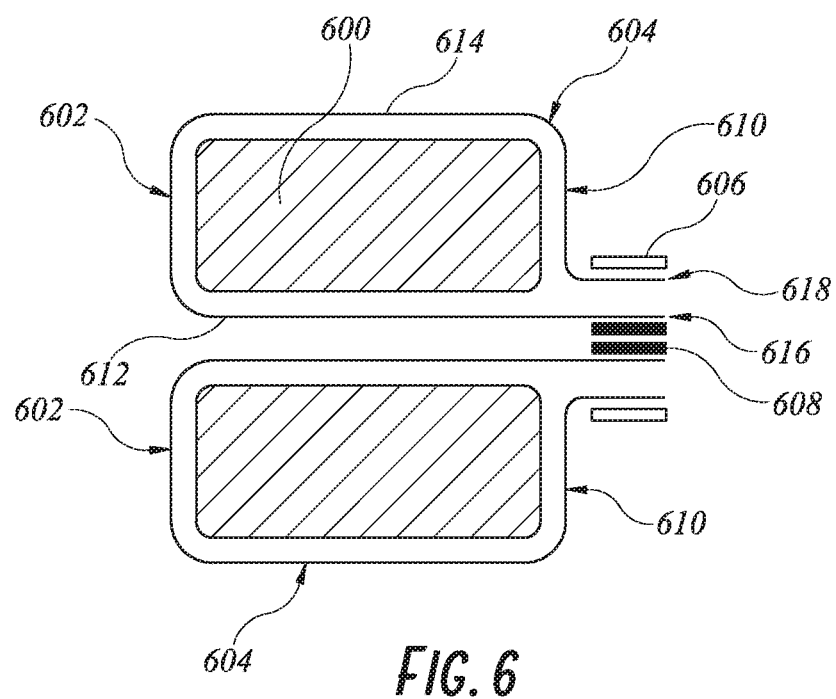
FIG. 6 shows a longitudinal cross section of a foam plug embodiment.
Figure 7:
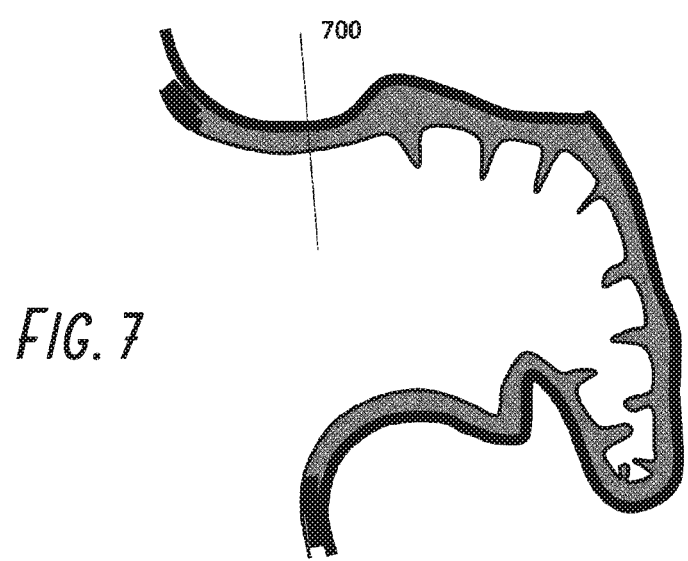
FIG. 7 shows an LAA cross section.
Figure 8:
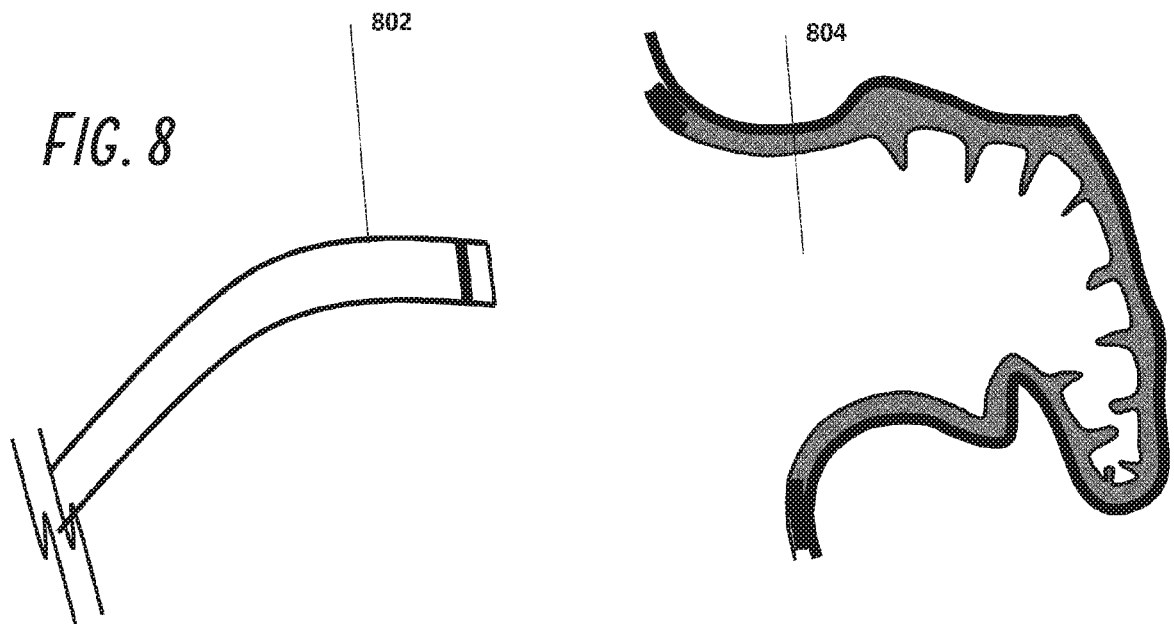
FIG. 8 is a schematic illustration of a guide catheter approaching the ostium to the left atrial appendage.
Figure 9:
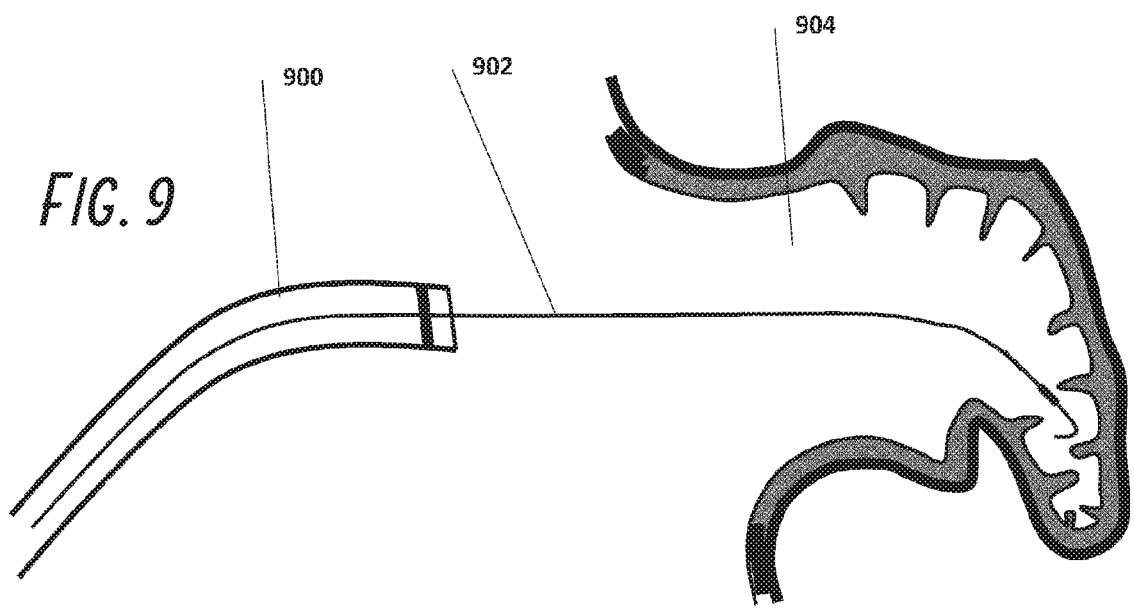
FIG. 9 is an illustration as in FIG. 8, with a guidewire placed within the left atrial appendage.
Figure 10:
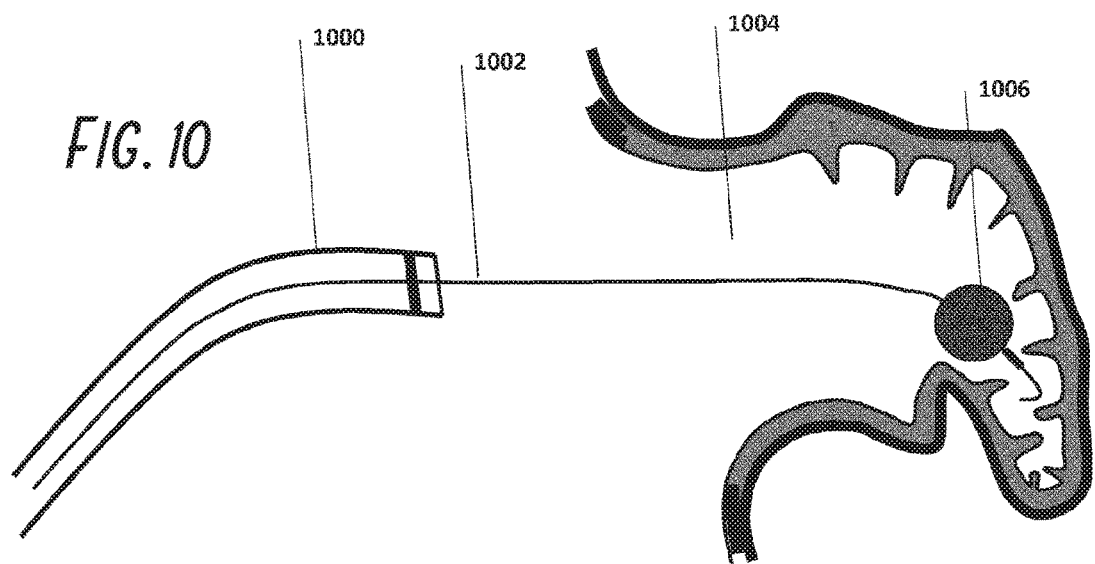
FIG. 10 is an illustration as in FIG. 9, with an inflatable balloon at the distal region of the guidewire positioned within the left atrial appendage.
Figure 11:
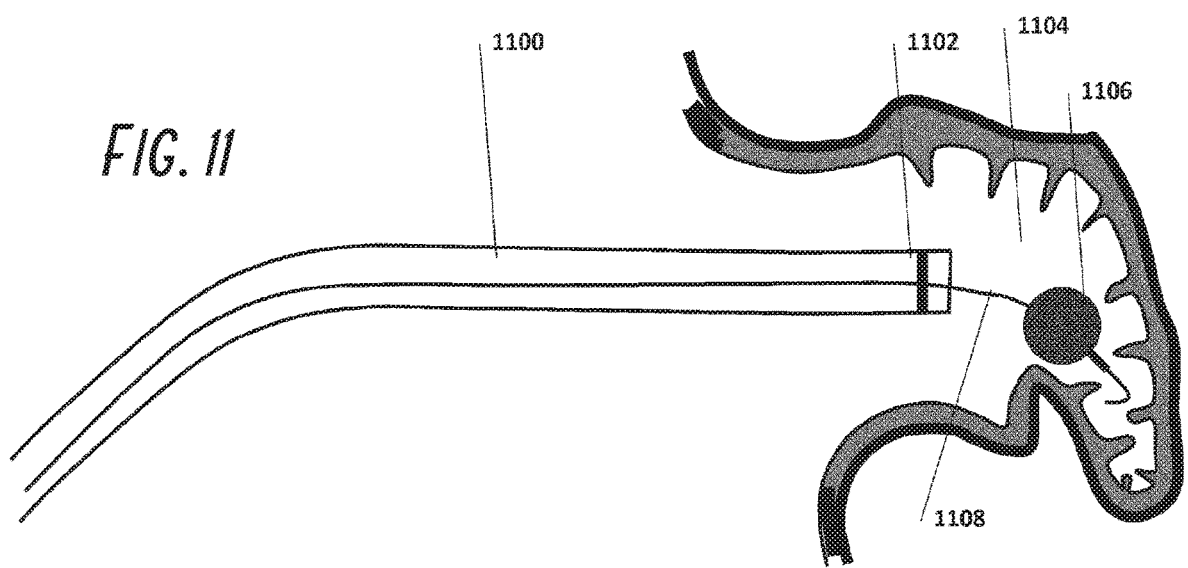
FIG. 11 is an illustration as in FIG. 10, with the guide catheter advanced distally along the guidewire and into the left atrial appendage.

A cross section of one embodiment is shown in FIG. 6 with foam plug 600 and the left atrium face 602 and the LAA face 610. The ePTFE material 604 encapsulates the foam plug 600 and its open ends are connected with an attachment structure such as a wire, suture or tubular crimp 606 over an inner tube 608. The inner tube 608 may be made of an implant grade stainless steel such as 304 or 316 grades or a cobalt-chromium alloy such as MP35n and the crimp 606 may be made of annealed 304 or 316 stainless steel or a cobalt-chromium alloy such as MP35n. This crimp also serves as an element which can be snared should the device need to be removed.

Referring to FIG. 6, the tubular ePTFE layer 604 extends along an inner layer 612 which lines the guidewire lumen, and everts out around the left atrial face 602 to form outer layer 614. A first end 616 of inner layer 612 is disposed concentrically within a second end 618 of outer layer 614. The first end 616 and second end 618 are clamped between inner tube 608 and outer crimp 606. In this manner, the implant can be encapsulated in a manner that presents a seamless left atrial face 602, and preserves the integrity of the guidewire lumen with inner tube 608.

Placement of the device is shown in FIG. 7 through 15. To close the left atrial appendage, the left atrium (LA) must first be accessed from the venous system. One approach is to use a Brockenbrough-style needle to puncture the atrial septum to access the LA from the right atrium (RA). The basic needle-puncture technique is performed obtaining venous access typically via the right femoral vein. A Mullins sheath and dilator are then tracked over a 0.025" or 0.032" guide wire previously placed in the superior vena cava (SVC). Fluoroscopic and echocardiographic imaging, such as transesophageal echo (TEE) or intracardiac echo (ICE), are typically utilized. If echo is not utilized, it is common to also place a pigtail catheter in the aortic root to define the location of the aortic valve, a step not necessary when using echo.

Once the Mullins sheath and dilator are in the SVC, the guide wire is removed and a trans-septal needle is placed through the dilator. The needle contains a stylette to prevent skiving off of polymeric material from the dilator lumen as it traverses to the tip. Once the needle is near the dilator tip, the stylette is removed and the needle is connected to a manifold and flushed. The Mullins sheath/dilator set and the needle (positioned within the dilator tip) are retracted into the SVC toward the RA as a unit. As the system is withdrawn down the wall of the SVC into the RA and positioned in the fossa ovale, the preferred puncture location.

Once proper position in the fossa ovale is observed, the needle is advanced across the fossa ovale into the LA. Successful trans-septal puncture can be confirmed by echo, pressure measurement, $O_2$ saturation and contrast injection. Once the needle position is confirmed to be positioned in the LA, the sheath and dilator can be advanced over it into the LA. In some cases, the user will first pass a guide wire through the needle into the LA and into an upper pulmonary vein (typically the left) prior to crossing. Alternative options include the use of radiofrequency trans-septal needles, which are useful for crossing very thick or hypertrophic septa, or the use of a safety wire placed through the needle and utilized for the initial puncture.

Referring to FIGS. 8 through 15, a guide catheter 802 is placed through the femoral vein into the right atrium of the heart and across the intra-atrial septum into the left atrium as described above and positioned near the LAA ostium 804. A guidewire 902 usually of 0.035" diameter is placed through guide catheter 900 and into the LAA 904. This guidewire 1002 may have attached to its distal end a balloon 1006 which is inflated in the LAA and serves as a bumper to prevent guide catheter 1100 from perforating the wall of the LAA. The guide catheter 1100 is then advanced over the guide wire 1108 into the LAA 1104. A radiopaque marker 1102 is used to guide catheter placement under fluoroscopy. The foam plug 1204 is then pushed through the guide catheter 1200 with pusher 1202 and is shown exiting the guide catheter 1300 slowly in FIG. 13 until it is fully deployed as shown in FIG. 14. The foam plug 1404 position may then be adjusted in place using the distal balloon 1408 and the guide catheter 1400, sliding the foam plug proximally by pulling on the balloon 1408 through shaft 1412 or sliding it distally by pushing guide catheter 1400 distally. The guide wire may also contain a pressure sensor within it such that sealing of the LAA is monitored and confirmation of a sufficient seal is made. Once the user is happy with the placement, the adhesive 1514 may be injected and/or mechanical anchors be deployed anchoring the plug to the wall. The guide wire balloon 1508 is deflated, after which the guide wire is removed. In an alternative embodiment, a binary adhesive system can be used where one component of the binary system is bonded to the outer surface of the skin covering the foam plug. The second component can be injected at the interface between foam plug and the wall of the LAA such that bonding happens only at the interface minimizing the risk of adhesive embolization.

Figure 12:
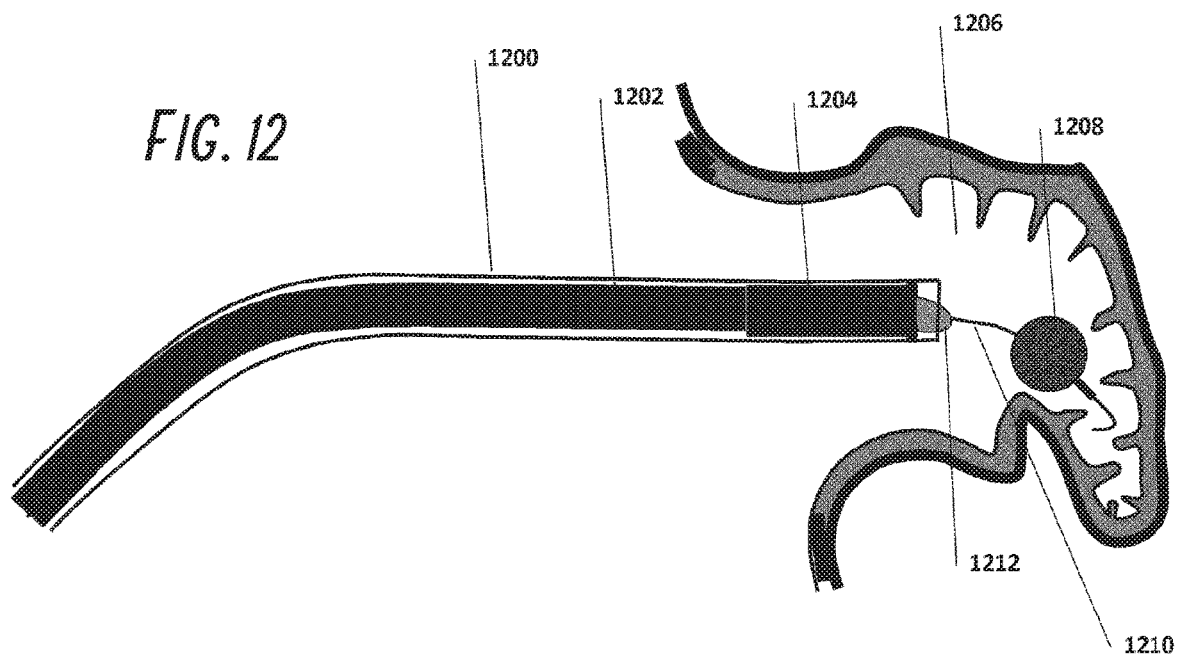
FIG. 12 is an illustration as in FIG. 11, showing the occlusion device and pusher positioned within the guide catheter.
Figure 13:
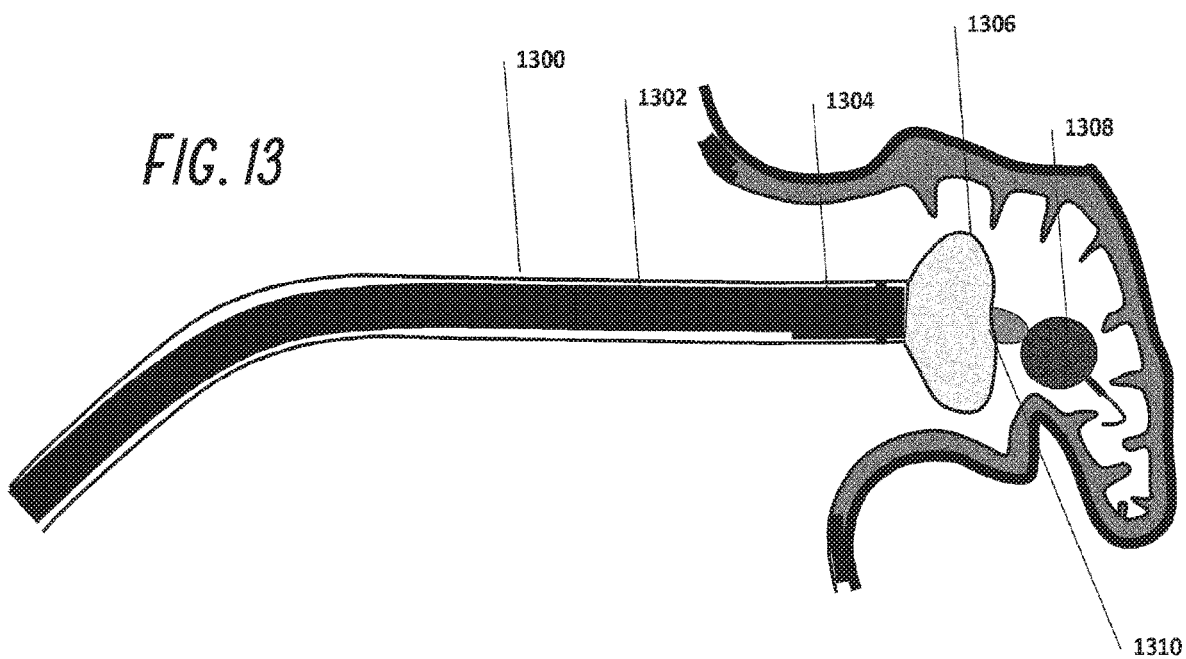
FIG. 13 is an illustration as in FIG. 12, showing the occlusion device partially deployed exiting the guide catheter.

An alternative to pushing the plug through the entire length of the guide catheter is that the plug 1204 may be initially located at the distal end of the guide catheter 1200 as shown in FIG. 12. The guidewire 1210 passes through the center of the plug 1204 and in this mode, the pusher 1202 only needs to push the plug a short ways to deploy it into the LAA.

For alternative anchors, they may be deployed, the shafts disconnected and removed. Disconnection mechanisms may be any of several types, such as threaded, electrolytic detachment, or others known in the art. In some embodiments, a suture attachment may be implemented, for example as described with respect to FIG. 24.

Figure 16:
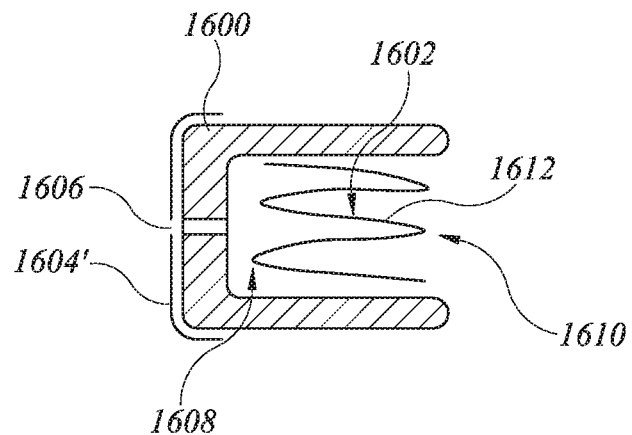
FIG. 16 shows a plug occlusive device in longitudinal cross section using metal and foam.

Alternative plug concepts include a combination of foam and metal implant as shown in FIG. 16. The foam 1600 is designed to provide ingrowth of tissue and also to provide a cushion of the metal stent 1602 onto the tissue of the LAA. The proximal face 1604' of the plug is covered in ePTFE, polyester or another thromboresistant tissue scaffold material to facilitate sealing with the desired pore size to encourage overgrowth. Stent 1602 could be made of Nitinol to enable it to pack into a 10, 12, 14, 16, 18 or 20F delivery catheter and expand to its desired diameter. It could be braided, laser cut or wire formed. Any of a variety of stent wall patterns may be utilized, depending upon the desired performance. The stent may be a balloon expandable stent, or self-expandable stent as are understood in the art. In the illustrated embodiment, a self-expandable stent 1602 comprises a plurality of proximal apexes 1608 and distal apexes 1610 connected by a plurality of zig zag struts 1612. A hole 1606 allows passage of the guidewire for delivery. This design may be advantageous in that the expansion force exerted by the plug on the LAA can be controlled separately from the foam characteristics. Also, it may be easier to pack this concept into a smaller geometry. For example, the plug can be packed into a smaller geometry by reducing the amount of foam that must be compressed into the delivery catheter while maintaining sufficient dilation force.

Alternatively, the foam plug may be constructed of 2 foams. One denser core to provide force, for example radial force, and an outer softer foam to engage the tissue irregularities. The softer foam could also be located on the proximal and/or distal ends to facilitate retrieval.

Figure 17:
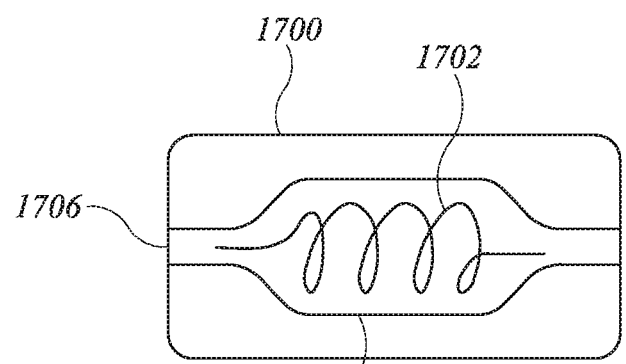
FIG. 17 shows a plug using metal coils and foam.

Another means of adding stiffness to the foam plug is shown in FIG. 17 where a cavity 1704 in the foam plug 1700 is made and a coil of wire 1702 may be advanced from the guide catheter at the proximal end 1706 into the cavity 1704. As the wire enters the cavity, it expands to its predetermined size and exerts force on the foam radially outwards. The type and amount of wire may be determined in vivo using x-ray guidance to examine the radial expansion of the foam into the LAA.

Instead of wires as shown in FIG. 17, a balloon may be passed into the foam and inflated to provide radial force while the outer foam serves to engage the tissue irregularities and tissue ingrowth. Following inflation, the balloon may be detached from a deployment catheter and the deployment catheter withdrawn. The balloon is preferably provided with a valve, to prevent the escape of inflation media. Inflation media may be any of a variety of media which is convertible between a first, flowable state and a second, hardened state such as by cross linking or polymerization in situ.

Figure 18:
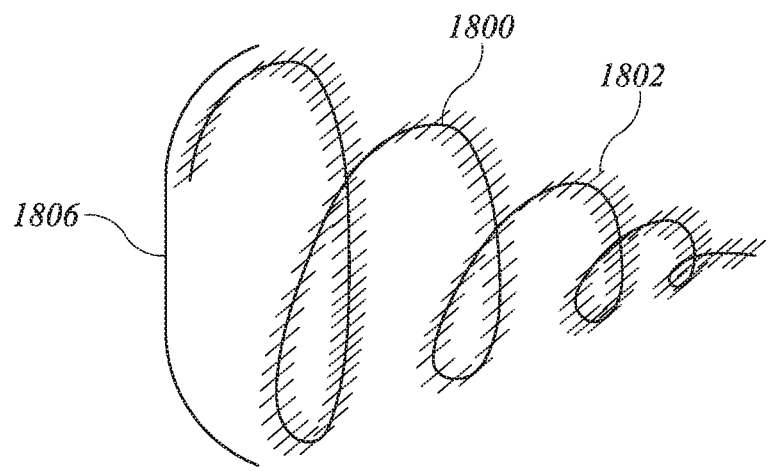
FIG. 18 shows a plug using a single metal coil.

Another LAA plug is shown in FIG. 18 as a spring like implant wire 1800 that is covered with foam 1802 to encourage ingrowth. The proximal face of the implant is covered with a sheet of ePTFE or other tissue scaffolding material. This implant may be stretched out for delivery and released in place.

Rather than using a foam, a low porosity outer bag without perforations could be placed in the LAA and then filled with a substance to provide the radial expansion. This substance may be a hydrogel, cellulose or polyvinylacetate.

Figure 19:
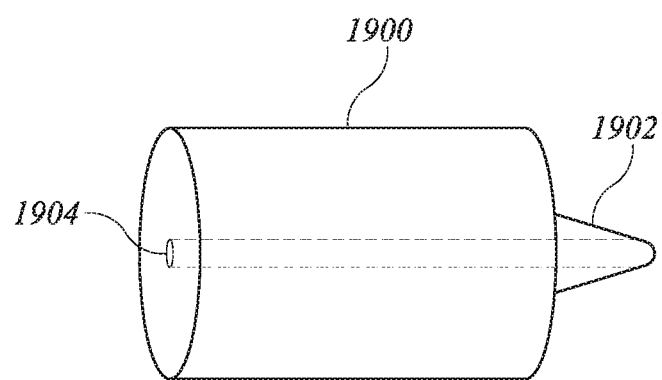
FIG. 19 shows a plug with a dilating distal tip.

Rather than requiring the use of a separate dilation device to cross the septum, the distal crimp element 1902 may be formed in a tapered manner such that it extends from the distal end of the catheter 1200 and serves as a dilating tip to dilate the opening in the septum as the catheter is advanced. See FIG. 19.

Figure 22:
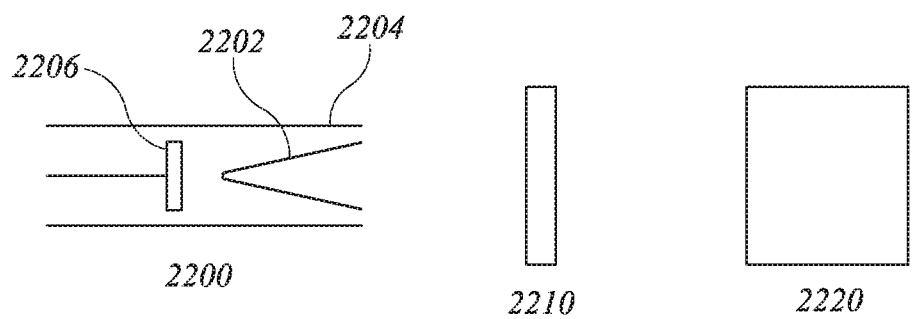
FIG. 22 shows the delivery of an expanding foam system.

An alternative plug design uses a foam such as cellulose sponge material that is compacted and dehydrated such that it can be packed into the guide catheter. This foam material 2202 may be packed into the guide catheter as shown in FIG. 22. The foam plug 2202 is then advanced from the distal end of the guide catheter 2204 with a plunger 2206 into the LAA. The plug exits the guide catheter and opens to a disc shape 2210. As the foam absorbs fluid in the blood, its length expands to form a cylinder 2220 filling the LAA. Expansion ratios for compressed cellulose materials may be as high as 17:1, expanded to compressed length.

Figure 23:
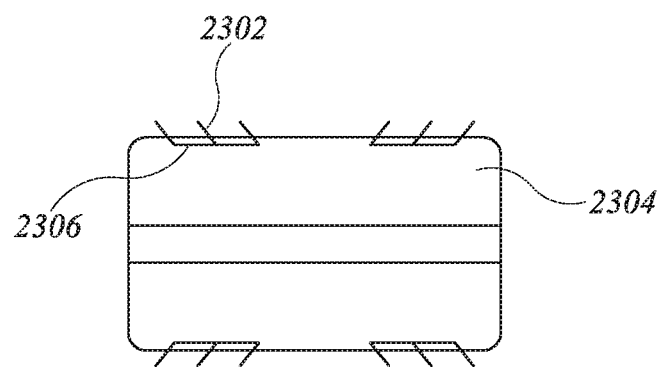
FIG. 23 shows a plug with barbs.

It may be advantageous to use small barbs 2302 in FIG. 23 to further engage the plug 2204 into the LAA. Barbs may be unidirectional or bidirectional to resist movement in either the proximal or distal direction. These barbs are embedded into the foam plug and may be 0.1 to 1 mm in height. It may be desirable to place the plug then engage the barbs as a secondary step. One such embodiment could include a multitude of nitinol barb wires with a ball or catch welded proximal to the barb tip. These could be gathered with the delivery catheter within a sleeve or suture then released when the ideal plug position has been confirmed.

Figure 24:
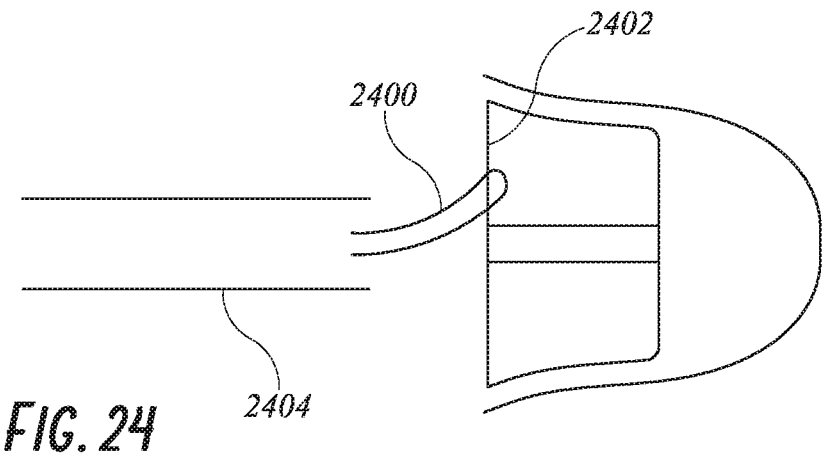
FIG. 24 shows a plug with a retrieval suture attachment.

One means of removing a device that is not functioning properly is to releasably attach a retrieval suture 2400 to the implant, such as to the proximal cap 2402 which also passes proximally throughout the entire length of the guide catheter 2404 in FIG. 24. If the device is to be removed, pulling on both ends of the suture 2400 will pull the outer covering into the guide catheter 2404 which can then be removed from the patient. If the device is properly placed, the suture 2400 may be cut and removed leaving the plug in place.

Deployment of the occlusion device has been discussed primarily in the context of a transvascular access. However, implants of the present invention may alternatively be deployed via direct surgical access, or various minimally invasive access pathways (e.g. jugular vein). For example, the area overlying the xiphoid and adjacent costal cartilage may be prepared and draped using standard techniques. A local anesthetic may be administered and skin incision may be made, typically about 2 cm in length. The percutaneous penetration passes beneath the costal cartilage, and a sheath may be introduced into the pericardial space. The pericardial space may be irrigated with saline, preferably with a saline-lidocaine solution to provide additional anesthesia and reduce the risk of irritating the heart. The occlusion device may thereafter be introduced through the sheath, and through an access pathway created through the wall of the LAA. Closure of the wall and access pathway may thereafter be accomplished using techniques understood in the art.

Depending upon the desired clinical performance, any of the LAA occlusion devices of the present invention may be provided with a drug or other bioactive agent, which may be injected via the deployment catheter, or impregnated within the open cell foam or coated on the implant. The bioactive agent may be eluted or otherwise released from the implant into the adjacent tissue over a delivery time period appropriate for the particular agent as is understood in the art. Useful bioactive agents can include those that modulate thrombosis, those that encourage cellular ingrowth, through-growth, and endothelialization, and potentially those that resist infection. For example, agents that may promote endothelial, smooth muscle, fibroblast, and/or other cellular growth into the implant including collagen (Type I or II), heparin, a combination of collagen and heparin, extracellular matrix (ECM), fibronectin, laminin, vitronectin, peptides or other biological molecules that serve as chemoattractants, molecules MCP-1, VEGF, FGF-2 and TGF-beta, recombinant human growth factors, and/or plasma treatment with various gases.

Anti-thrombotics can typically be separated into anti-coagulants and anti-platelet agents. Anti-Coagulants include inhibitors of factor(s) within the coagulation cascade an include heparin, heparin fragments and fractions as well as inhibitors of thrombin including hirudin, hirudin derivatives, dabigatran, argatroban and bivalrudin and Factor X inhibitors such as low molecular weight heparin, rivaroxaban, apixaban.

Antiplatelet agents include GP 2b/3a inhibitors such as epifibitide, and abciximab, ADP Receptor agonists (P2/Y12) including thienopyridines such as ticlopidine, clopidogrel, prasugrel and tacagrelor and aspirin. Other agents include lytic agents, including urokinase and streptokinase, their homologs, analogs, fragments, derivatives and pharmaceutical salts thereof and prostaglandin inhibitors.

Antibiotic agents can include, but are not limited to penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Biologic agents as outlined above maybe be added to the implant 204 and may be injected through the delivery catheter into the space between the proximal cap 206 and the foam plug 204. This may serve as a reservoir to minimize thrombus formation during the initial implantation and reduce the need for systemic anticoagulation following device implantation.

An electronic pressure sensor may be embedded into the proximal end of the foam plug which may be used to transmit LA pressure to a remote receiver outside the body for the monitoring of LA pressure which is useful to monitor cardiac function. In addition, a cardiac pacer or defibrillator may be embedded into the foam plug and attached electrically to the distal anchor. A drug delivery reservoir may be embedded with connection to the LA for controlled delivery of biologic agents as outlined above.

Figure 25A:
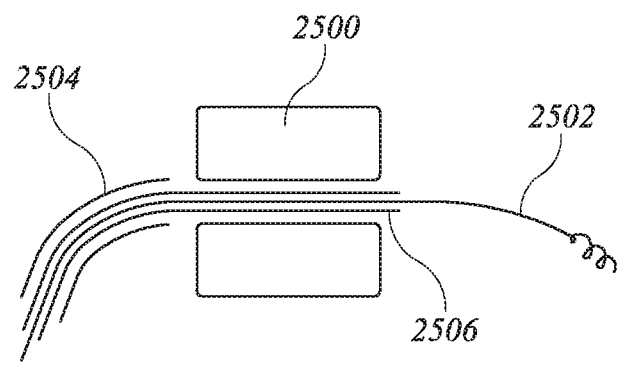
FIGS. 25A and 25B show a distal anchoring system.
Figure 25B:
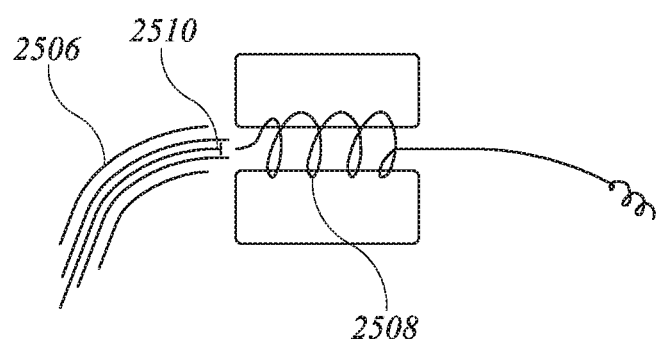

Another means of anchoring is shown in FIG. 25A where the foam plug 2500 is placed in the LAA. The distal screw lead 2502 is advanced and screwed into the LAA wall. Guide 2506 is pulled proximally as shown in FIG. 25B. When this guide 2506 is pulled back, the screw lead wire, made of Nitinol, bunches up into a "birds nest" 2508 or forms a coil inside the foam plug 2500. The screw lead wire 2502 is pushed distally from the guide catheter 2504 with a pusher 2510 and continues to bunch up into the foam. The catheter system 2504, 2506 and 2510 are then removed.

Figure 26:
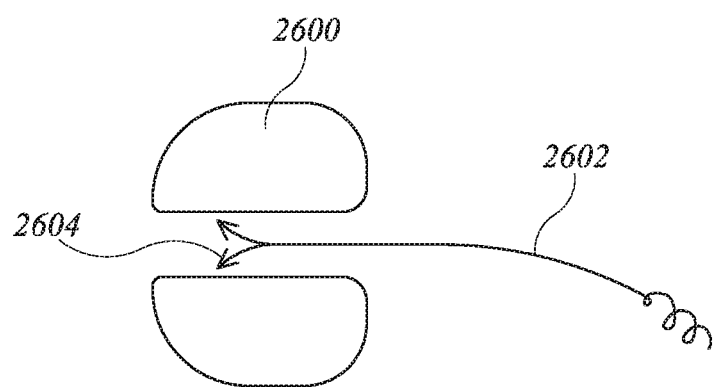
FIG. 26 shows an alternative distal anchoring system.

Another means of anchoring the distal anchor element to the foam is shown in FIG. 26. Two barbed leads 2604 are attached to anchor 2602 such that when advanced into place in the foam plug 2600, the barbs 2604 dig into the foam plug.

FIGS. 27A-27G are various views of an embodiment of a device 10 for occlusion of the left atrial appendage (LAA). The device 10 may include the same or similar features as other devices for occlusion of the LAA described herein, such as the plug 204, and vice versa. The device 10 includes an internal locking system 101 for securing the device 10 within the LAA. In some embodiments, the device 10 may not include the internal locking system 101 or other anchoring features, for example the device 10 may be anchored by tissue ingrowth alone. The occlusion device 10 comprises an expandable media such as an open cell foam body 15, for example a plug. The body 15 enables collapse and expansion of the device 10 and also enhances ingrowth of tissue into the foam.

Figure 27F:
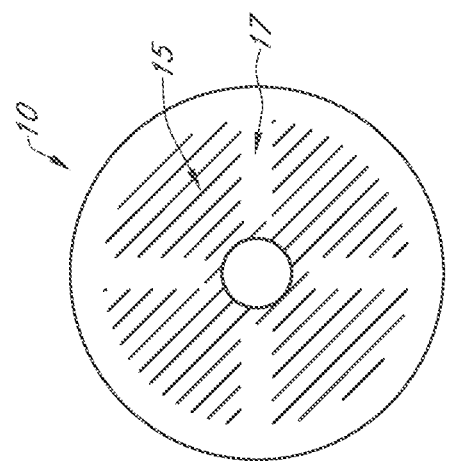
Figure 27E:
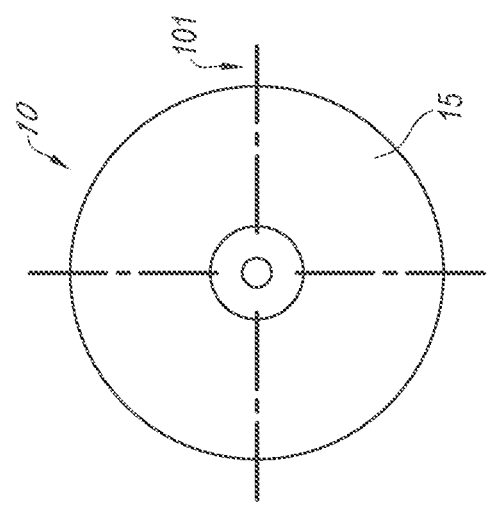
Figure 27D:
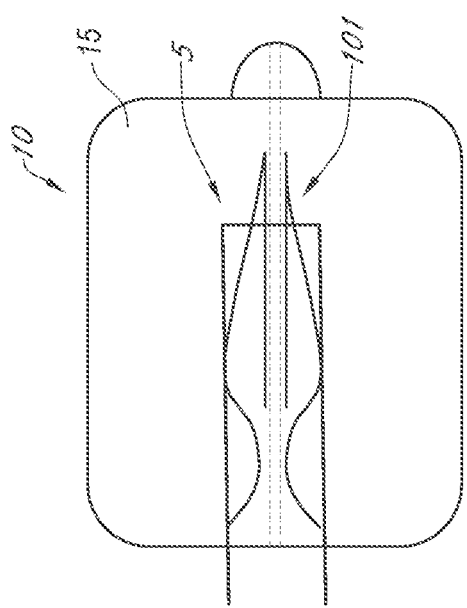
Figure 27G:
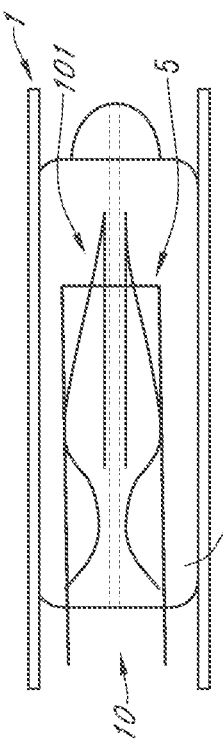

The body 15 of the device 10 shown in FIG. 27A through FIG. 27F is in its expanded configuration. The body 15 is in a compressed configuration in FIG. 27G. The device 10 includes the foam body 15, a skin 20, a central lumen 25, a finial 30, and a dynamic internal locking system 101 which anchors the device 10 within the LAA. FIG. 27A is a side cross-section view of the device 10 showing the body 15 and the internal locking system 101 in a deployed configuration. FIG. 27B is an end view of the proximal end of the device 10 showing the body 15 and the internal locking system 101 in a deployed configuration. FIG. 27C is a side view of the device 10 showing the body 15 and the internal locking system 101 in a deployed configuration. FIG. 27D is a side cross-section view of the device 10 showing the body 15 in a deployed configuration and the internal locking system 101 in a constrained configuration. FIG. 27E is an end view of the distal end of the device 10 showing the body 15 and the internal locking system 101 in a deployed configuration. FIG. 27F is a cross-section view of the device 10 taken along the line 1F-1F as shown in FIG. 27C. FIG. 27G shows the body 15 and internal locking system 101 loaded and compressed within a delivery sheath 1. The device 10 may be delivered via a delivery catheter in the configuration shown in FIG. 27G. The body 15 of the device 10 may then expand with the internal locking system 101 still constrained, as shown in FIG. 27D. The internal locking system 101 may then deploy into the deployed configuration as shown in FIG. 27A.

FIG. 27G shows the body 15 and internal locking system 101 loaded and compressed within an embodiment of a delivery sheath 1. In some embodiments, the delivery sheath 1 may be an outer delivery catheter. The body 15 and internal locking system 101 are loaded and compressed within a delivery catheter 5. The device 10 may be entirely or partially inside the delivery catheter 5. In some embodiments, the delivery catheter 5 may be an inner delivery catheter. The device 10 may be loaded and compressed with the delivery catheter 5 inside of the delivery sheath 1. Removing the delivery sheath 1, for example by retracting the delivery sheath 1 in the proximal direction, may allow the body 15 of the device 10 to expand. The body 15 expands while the internal locking system 101 is still constrained, for example by the delivery catheter 5. FIG. 27D shows the body 15 in its deployed state, with the internal locking system 101 in a constrained configuration within the delivery catheter 5. This demonstrates the first step in the deployment process, specifically placement of the device 10 within the LAA where the body 15 is expanded and the internal locking system 101 is constrained and thus the anchors are not deployed. The second step of the deployment process is shown in FIG. 27A where the internal locking system 101 has been deployed through the body 15. In some embodiments, this second step is reversible to retract the anchors, for example if placement of the device 10 within the LAA is unacceptable. The internal locking system 101, for example an anchoring component or system as further described herein, is deployed from within the body 15 to deploy at least one and in some implementations at least 2 or 4 or 6 or more anchors of the internal locking system 101 outside the body 15 to engage adjacent anatomy of the LAA.

The internal locking system 101 may be controllably deployed a period of time after the body 15 expands. For instance, the location, orientation, etc. of the device 10 may be verified with various imaging techniques such as by fluoroscopy with injection of contrast media via the central lumen before the internal locking system 101 is deployed and the anchors secure the device 10 within the LAA. In some embodiments, even after deployment of the internal locking system 101 and anchors thereof, the anchors may be retracted to a position within the body 15 for repositioning, and/or retrieval of the device 10 from, within the LAA.

FIG. 27F shows an embodiment of the device having slots 17. The slots 17 are formed within the foam body 15. For instance, material of the foam body 15 may be removed to facilitate deployment of the internal locking system 101, such as outward expansion of anchors to engage the tissue.

The device 10 may have any or all of the same or similar features and/or functionalities as the other plugs described herein, for example the plug 204, etc. For example, the device 10 is at least partially encapsulated within the skin 20. In some embodiments, the skin 20 may cover the proximal end of the body 15. The skin 20 may be a thin, strong outer layer. The skin 20 may be a thin, encapsulating layer. The skin 20 may be fabricated from ePTFE (expanded polytetrafluoroethylene), polyolefin, polyester, other suitable materials, or combinations thereof. In some embodiments, the skin 20 may be fabricated from bioabsorbable materials, for example polylactic acid (PLA), Polyglycolic acid (PGA), ploycaprolactone (PCL), PHA, collagen, other suitable bioabsorbable materials, or combinations thereof. The skin 20 can be oriented or otherwise modified to be elastomeric in at least one direction, such as radially.

The body 15 may be made of polyurethane, polyolefin, PVA, collagen foams or blends thereof. One suitable material is a polycarbonate-polyurethane urea foam with a pore size of 100-250 um and 90-95% void content. The body 15 may be non-degradable or use a degradable material such as PLA, PGA, PCL, PHA, and/or collagen. If degradable, the tissue from the LAA will grow into the foam body 15 and replace the foam over time. The body 15 may be cylindrical in shape in an unconstrained expansion but may also be conical with its distal end smaller than the proximal end, or vice versa. The body 15 may also be oval in cross section to better match the opening of the LAA.

The device 10 is oversized radially in an unconstrained expansion to fit snuggly into the LAA. The device 10 may be 5-50 millimeters (mm) and generally at least about 10 mm or 15 mm in diameter in its unconstrained configuration, for example depending on the diameter of the target LAA. The length "L" of the device 10 may be less than, similar to or greater than its diameter "D" such that the L/D ratio is less than 1.0, about or greater than about 1.0, greater than about 1.5, or greater than about 2.0. The L/D ratio may be greater than 1.0 to maximize its stability. However, in some embodiments, the L/D ratio may be less than 1.0, for example, from about 0.2 to about 0.9, or from about 0.3 to about 0.8, or from about 0.4 to about 0.6. The compliance of the material of the device 10 is designed such that it pushes on the walls of the LAA with sufficient force to maintain the plug in place but without overly stretching the LAA wall. The foam body 15 and/or skin 20 also conforms to the irregular surfaces of the LAA as it expands, to provide a complementary surface structure to the native LAA wall to further enhance anchoring and promote sealing. Thus, the expandable foam body 15 conforms to the native irregular configuration of the LAA. In some embodiments, the structure of the foam body 15 may be fabricated such that axial compression on the opposing ends of the body 15 such as by proximal retraction of a pull wire or inner concentric tube causes the foam to increase in diameter.

The body 15 and/or skin 20, for example the foam material and/or ePTFE, may be provided with one, two or more radiopaque markers, such as radiopaque threads 210 (see FIG. 2) or filled with or impregnated with a radiopaque filler such as barium sulfate, bismuth subcarbonate, or tungsten, which permit the operator to visualize under x-ray the device 10 for proper positioning in the anatomy. Visualization of the device 10 may be used to verify the position of the device 10 before deployment of anchors to secure the device 10 in place.

The skin 20, such as an outer ePTFE layer, may have a thickness between about 0.0001 inches and about 0.0030 inches. In some embodiments, the thickness of the skin 20 may be between about 0.0003 inches and about 0.0020 inches. In some embodiments, the thickness of the skin 20 may be between about 0.0005 inches and about 0.0015 inches. The thickness of the skin 20 may be uniform, for example the same or approximately the same no matter where the thickness is measured. In some embodiments, the thickness of the skin 20 may be non-uniform, for example the thickness may be different in different portions of the skin 20.

The skin 20, such as an outer ePTFE layer, may also serve as the blood contacting surface on the proximal end of the device 10 facing the left atrium. The skin 20 may have pores or nodes such that blood components coagulate on the surface and an intimal or neointimal covering of tissue grows across it and anchors tightly to the skin material. Pore sizes may be within the range of from about 4μ to about 110μ. In some embodiments, the pore sizes are within the range of from about 30μ to about 90μ. In some embodiments, the pore sizes are within the range of from about 30μ to about 60μ. Such ranges of pore sizes are useful for formation and adherence of a neointima. In some embodiments, the skin 20, such as an outer ePTFE layer, may be formed from a tube with a diameter about the same diameter of the foam body 15. and allows one to collapse and pull on the body 15 without tearing the foam material.

The skin 20 may be constructed of materials other than ePTFE such as woven fabrics, meshes or perforated films made of FEP, polypropylene, polyethylene, polyester or nylon. The skin 20 may have a low compliance (e.g. non-elastic), for instance a low compliance longitudinally, may be sufficiently strong as to permit removal of the plug, may have a low coefficient of friction, and/or may be thromboresistant. The skin 20 serves as a matrix to permit plug removal as most foams are not sufficiently strong to resist tearing when pulled. The body 15 can also be coated with or contain materials to enhance its ultrasonic echogenic profile, thromboresistance, lubricity, and/or to facilitate echocardiographic visualization, promote cellular ingrowth and coverage.

The skin 20 may include holes to permit contact of the LAA tissue with the foam body 15. Exposure of the foam body 15 to the LAA or other tissue has benefits for example encouraging ingrowth of tissue into the foam plug pores and/or increasing friction to hold the body 15 in place. These holes may be 1 to 5 mm in diameter or may also be oval with their long axis aligned with the axis of the foam plug, the length of which may be 80% of the length of the foam plug and the width may be 1-5 mm. The holes may be as large as possible such that the outer covering maintains sufficient strength to transmit the tensile forces required for removal. The holes may be preferentially placed along the device 10. In some embodiments, the holes are placed distally to enhance tissue ingrowth from the distal LAA wall.

In some embodiments, the device 10 includes an occlusion region and anchoring region. The proximal portion of the device 10 facing the left atrium after the device is implanted in the LAA may include the occlusion region. The occlusion region may be a blood contacting surface on the proximal end of the device 10 that is thromboresistant while promoting formation of a neointima at the occlusion region. The occlusion zone encourages thromboresistance and endothelialization from the blood and adjacent tissue. The anchoring zone promotes fast and tenacious tissue ingrowth into the device 10 from the adjacent non-blood tissue. The anchoring zone may be lateral surfaces of the device 10 that interface with tissue adjacent and/or within the LAA. The anchoring zone can also include the distal end of the device 10 that faces the distal wall of the LAA after implantation.

Figure 28B:
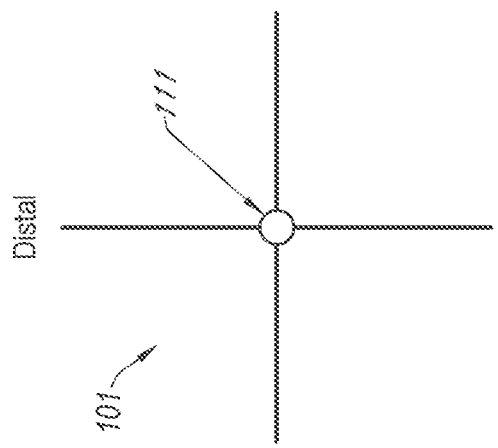
FIGS. 28A-28D are various views of an embodiment of an internal locking system that may be used with the various devices and plugs described herein for occlusion of the LAA, such as the device of FIGS. 27A-27G.
Figure 28D:
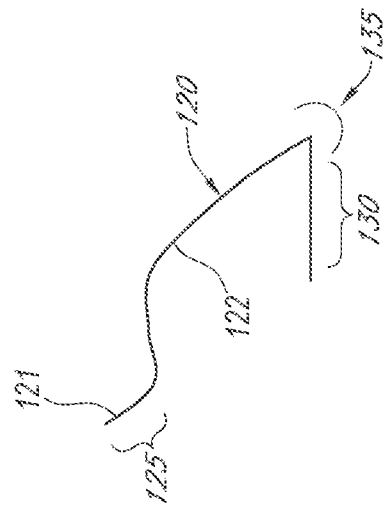
Figure 28A:
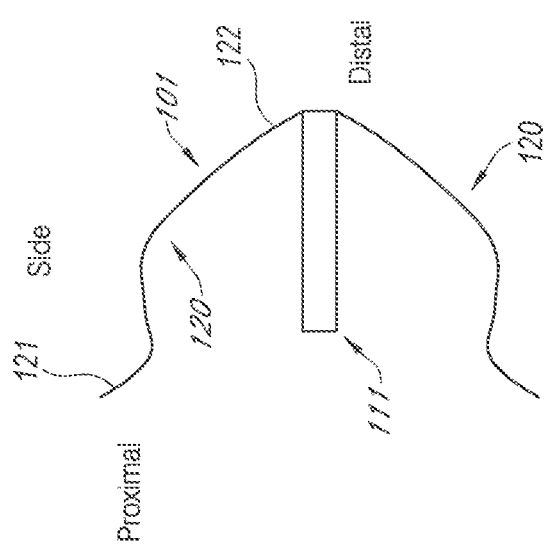
Figure 28C:
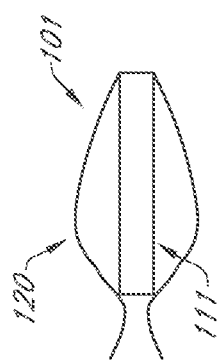

FIGS. 28A-28D are various views of an embodiment of an internal locking system 101 that may be used with the device 10. In some embodiments, multiple internal locking systems 101 may be used with the device 10. FIG. 28A is a side view of the internal locking system shown in a deployed configuration. FIG. 28B is an end view of a distal end of the internal locking system 101 in a deployed configuration. FIG. 28C is a side view of the internal locking system 201101 in a constrained configuration. FIG. 28D is a side view of an embodiment of an anchor 120 of the internal locking system 101.

Any of a variety of structures may be utilized as the dynamic internal locking system 101 with the device 10. In general, at least about two or four or six or more tissue anchors 120 may be actively or passively advanced from the implantable device 10 into adjacent tissue surrounding the implantation site. Following deployment of the device 10 and expansion of the body 15, a tissue engaging segment 121 of the tissue anchor 120 will extend beyond the skin by at least about one, and in some implementations at least about two or four 4 mm or more. The tissue engaging segment 121 is carried by a support segment 122 of the tissue anchor 120 which extends through the foam body 15, and may be attached to a deployment control such as a pull wire, push wire, tubular support or other control structure depending upon the desired configuration.

The locking system 101 discussed primarily herein is a passive deployment construction. Removal of a constraint allows the tissue anchors 120 to laterally self expand to deploy into adjacent tissue. Self expansion may be accomplished by constructing the tissue anchor 120 using nitinol, Elgiloy, stainless steel or other shape memory or spring bias materials. The constraint may be removed by proximal retraction or distal advance until the tissue anchors 120 are no longer engaged by the constraint, depending upon the construction of the locking system 101.

Alternatively, tissue anchors 120 may be deployed actively such as by distal advance, proximal retraction or rotation of a control, or inflation of a balloon positioned within the device 10 to actively drive the anchors 120 through the skin 20 or corresponding apertures on the skin 20 and into tissue. For example, a plurality of support segment 122, such as struts, may be joined at a distal end to a central hub 111, and incline radially outwardly in the proximal direction. Proximal retraction of the hub 111 will cause the tissue engaging segment 121 to advance along its axis beyond the skin 20 and into the adjacent tissue. The inclination angle of the support segment 122, for example the struts, may be reversed, in another construction, such that distal advance of the hub 111 will deploy the tissue engaging segments 121 beyond the skin 20. Proximal or distal advance of the hub 111 may be accomplished by proximal or distal advance of a control such as a control wire or inner tube releasably engaged with the hub 111.

Depending upon the desired clinical performance, the tissue anchors 120 may be retractable, such as by axial distal or proximal movement of the control depending upon the inclination angle of the anchors 120. In the embodiment primarily illustrated herein, re-sheathing the anchors 120 may be accomplished by advancing the tubular constraint along the ramped surface of the tissue anchor 120 to move the anchor 120 radially inwardly towards the central longitudinal axis of the device 10. In the case of an anchor 120 which deploys by advance along its own longitudinal axis, the anchor 120 may be retracted by advancing the control in the opposite direction from the direction advanced to deploy the anchors 120.

Referring to FIGS. 28A-28D, the internal locking system 101 includes a central tubular element or hub 111 and anchors 120. The anchors 120 may be arms, segments, or other members extending from the hub 111. Each anchor 120 may comprise a tissue engaging segment 121 and a support segment 122 which extends to the hub 111 or other control. The internal locking system 101 has a single central tubular hub 111 and a multitude of the anchors 120. As shown, there are four anchors 120. There may be two, three, four, five, six, seven, eight, or more anchors 120. The anchor 120 may be rotatably, hingedly, or otherwise moveably coupled with the hub 111. The anchor 120 may thus move relative to the hub 111, for example after being released from a restraint holding the anchor 120 in a constrained configuration to deploy into a deployed configuration. As further example, the anchor 120 may move from the deployed configuration to a retracted position, as further described herein. The anchor 120 may be curvilinear as shown, for example to allow the anchor 120 to take the geometry shown in FIG. 28A when unconstrained.

The illustrated anchor 120 may have a distal region 130, a hinge region 135, and/or a proximal region 125. The distal region 130 interacts with the hub element 111. The hinge region 135 and the curvilinear geometry as shown allow the end of the proximal region 125 to extend beyond the body 15, for example beyond a sidewall of the body 15. The proximal region 125 includes a tissue engaging segment 121 configured to engage adjacent tissue. The tissue engaging segment 121 may be the entire proximal region 125 or a portion thereof, for example the tip, etc. The proximal region 125 may thus include a sharpened tissue engaging segment 121, a shaped tissue engaging segment 121, an angled tissue engaging segment 121, a thickness configured for tissue engagement, and/or other suitable features. In some embodiments, the proximal region 125 may retract back within the body 15, as further described herein. In the embodiment shown, the anchor 120 and central tube 111 are distinct elements which are affixed to one another as shown. In other embodiments, the anchor 120 and tube 111 are a single, integral unit.

The internal locking system 101 is made from biocompatible metallic wire such as Nitinol, implant grade stainless steel such as 304 or 316, or cobalt-chromium based alloys such as MP35N or Elgiloy. In some embodiments, the internal locking system 101 may be cut from a single tubular piece of metal fabricated via machining or laser cutting followed by a secondary forming or annealing step using similar materials.

The internal locking system 101 may be in a constrained configuration as the device 10 is placed in position in the LAA and the body 15 expands therein. Then, in a secondary step, the internal locking system 101 locks or otherwise secures the device 10 in the LAA by engaging the anchors 120. If the position is not considered optimal, or if the device 10 otherwise needs to be repositioned within and/or removed from the LAA, the internal locking system 101 and anchors 120 thereof can be unlocked and the device 10 repositioned and/or removed.

FIGS. 29A-29B are sequential side views of an axially movable loop type unlocking mechanism that may be used with the device 10 to release the tissue anchors. FIG. 29A is a side cross-section view of the device 10 showing the tissue anchors of internal locking system 101 in a deployed configuration. FIG. 29B is a side cross-section view of the device 10 showing the tissue anchors in a retracted configuration. An embodiment of an unlocking system 140 is shown. The unlocking system 140 includes a ring 145. The ring 145 may be moved over the anchors 120 to move the anchors 120 to retracted configurations. The ring 145 may be moved by a pull rod 147. The ring 145 may be releasably attached to the pull rod 147. The pull rod 147 may extend through a catheter to engage the ring 145. The unlocking system 140 may be utilized if, after the internal locking system 101 is deployed, it is desirable to unlock the device 10 from within the LAA in order to reposition and/or remove the device 10.

In the illustrated construction, deployment of the tissue anchors by distal advance of the restraint enables reversible deployment, so that subsequent proximal retraction of the restraint will retract the tissue anchors. Alternatively, proximal retraction of the restraint to release the tissue anchors will irreversibly release the tissue anchors.

Figure 30:
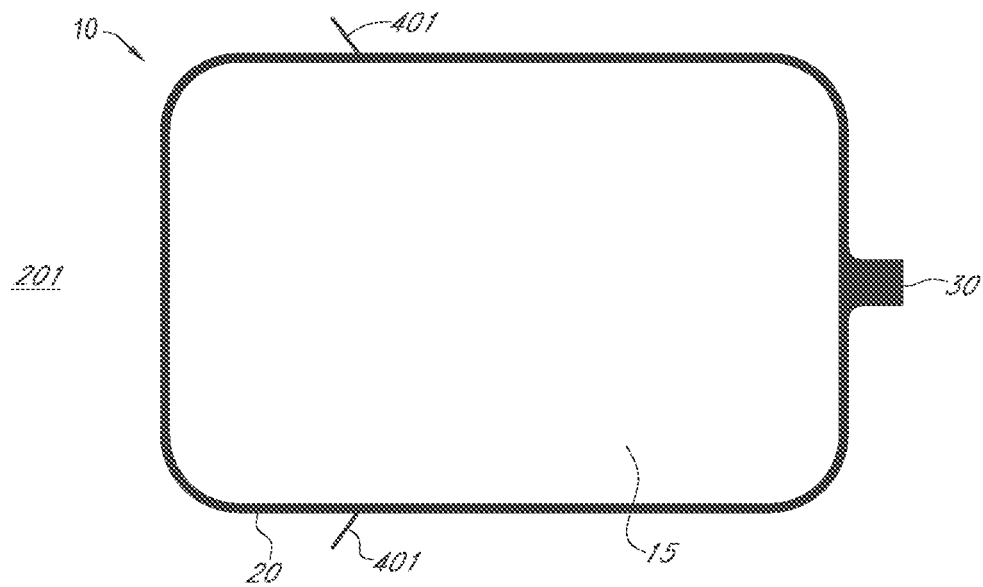
FIG. 30 is a side view of an embodiment of a device for occlusion of the LAA having flexible anchors.

FIG. 30 is a side view of an embodiment of the device 10 having flexible anchors 401. The device 10 shown in FIG. 30 may have the same or similar features and/or functionalities as the other devices for excluding the LAA described herein, and vice versa. The device 10 may be in the configuration shown in FIG. 30 adjacent to or within a left atrium (LA) 201. The device 10 in FIG. 30 includes the expandable body 15, such as an open cell foam body, which enables collapse and expansion of the device 10, and at least partially encased within the skin 20, which may be a thin, strong layer fabricated from ePTFE (expanded polytetrafluoroethylene), polyolefin, or polyester which assists with healing, anchoring, and retrieval. The device 10 may also be deployed, and, if desired, repositioned and/or retrieved, or the device 10 may be permanently fixated within the LAA by engaging an anchoring system, such as the internal locking system 101, as described herein. The anchors 401, which may be metallic, may be fabricated from Nitinol. The anchors 401 may be small diameter Nitinol wire approximately 0.001 inches to approximately 0.010 inches in diameter. In some embodiments, the anchors 401 may be approximately 0.0005 inches to approximately 0.020 inches in diameter. The anchors 401 may be deployed upon expansion of the body 15. For example, the anchors 401 may self-deploy upon deployment of the device 10 from a delivery catheter. The anchors 401 may be relatively short and extremely flexible. The anchors 401 may be unable to penetrate the tissue or cause any anchoring immediately after deployment of the device 10.

Figure 31:
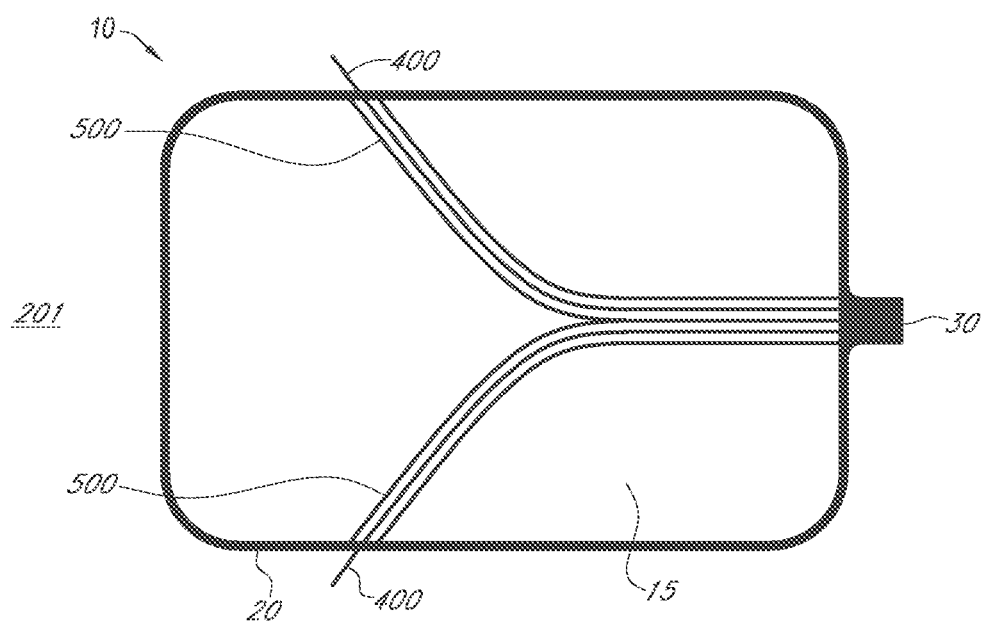
FIG. 31 is a side view of an embodiment of a device for occlusion of the LAA having flexible anchors, with stiffening tubular members in a pre-deployed configuration.

FIG. 31 is a side view of an embodiment of a device 10 for occlusion of the LAA having anchors 401 with tubes 500. The device 10 may be positioned adjacent to or within the left atrium (LA) 201. The anchors 401 may be flexible anchors, or in some embodiments the anchors 410 may be relatively stiffer, as further described. The tubes 500 may be stationary or moveable tubes, as further described. In some embodiments the tubes 500 are hypotubes. The tubes 500 may be stainless steel, polyamide, or other suitable materials. The tubes 500 may surround a corresponding anchor 401, as further described.

In some embodiments, the anchors 401 may be fixed such that they do not move axially. For example, the anchors 401 may have a portion, such as a tissue engaging segment 121, of a fixed length extending outside the body 15. The portion of the anchors 401 extending outside the body 15 may be bent when compressed within a delivery catheter and/or sheath, and these portions of the anchors 401 may then straighten out to the configuration shown in FIGS. 31 and 32 after deployment of the body 15. The fixed length portion of the anchors 401 extending beyond the body 15 may be from about 1 mm to about 5 mm, or from about 1.5 mm to about 4 mm, or from about 2 mm to about 3 mm. This length of exposed anchor 401 outside the body 15 may be effectively shortened by deployment of a corresponding tube 500, as further described. Deployment of the corresponding tube 500 about the corresponding anchor 400 may shorten the effective length of exposed anchor 401, i.e. the length of the anchor 401 extending beyond the end of the tube 500 after deployment of the tube 500, from about 0.5 mm to about 1 mm. These are merely examples of different lengths of the anchor 401 and other suitable lengths may be implemented.

In some embodiments, the anchors 401 may be moveable axially. For example, the anchors 401 may not deploy or otherwise extend outside the body 15 immediately upon expansion of the body 15. Following acceptable positioning of the device 10 within the LAA, the flexible anchors 401 may then be advanced through a corresponding tube 500. The anchors 401 may move axially in any suitable manner, including those described elsewhere herein. The anchor 401 may be moved through the tube 500 either before or after the tube 500 has been moved and deployed outside the body 15, as described below.

Figure 32:
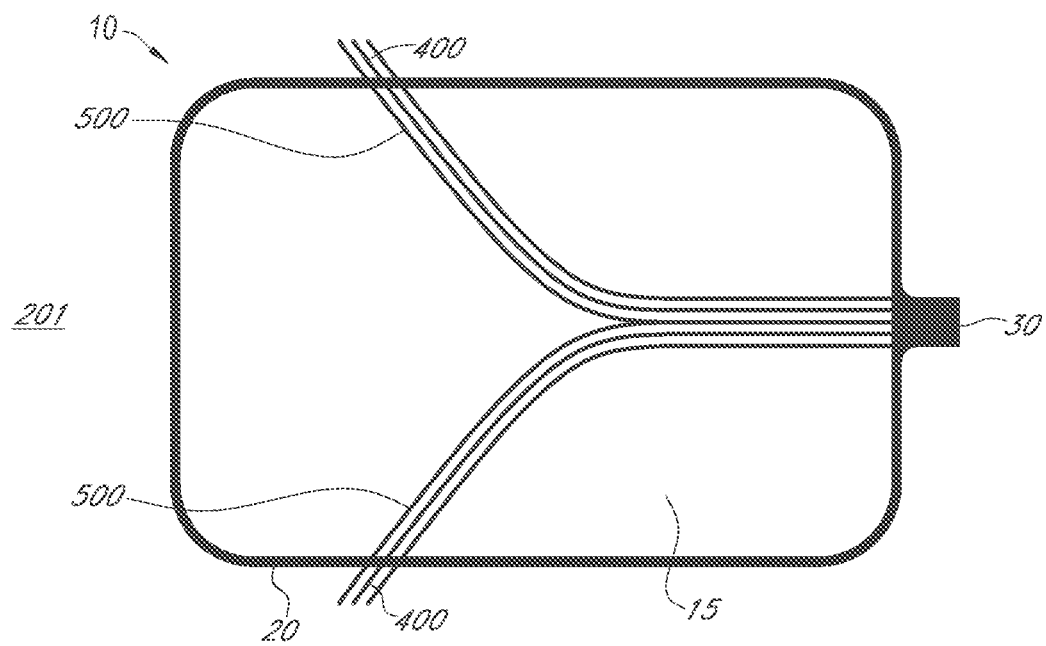
FIG. 32 is a side view of the device of FIG. 31, with the stiffening tubular members in a deployed configuration.

In some embodiments, the tubes 500 are moveable and deploy outside the body 15. The tubes 500 may be moveable in embodiments having either fixed or moveable anchors 401. The tubes 500 may be pre-loaded over corresponding wire anchors 401 as shown in FIG. 31, for example one tube 500 per anchor 401. The tube 500 may then be moved over the corresponding anchor 401 as shown in FIG. 32. The tube 500 may straighten the anchor 401 and add mechanical integrity. The tube 500 may also act as a perforation protector to prevent the anchor 401 from puncturing through the wall of the LAA. Movement of the tube 500 over the corresponding anchor 401 may shorten the exposed length of the anchor 401, as described. This may provide for a stiffer tissue engaging segment of the anchor 401 due to the shortened exposed length.

In some embodiments, the tubes 500 extend from the delivery catheter to or near the outer surface of the body 15 but do not extend outside the body 15. Instead, the tubes 500 just guide the anchor 401, for example around the curve, and support the wire 401 right up to tissue penetration. The tubes 500 may set the launch angle so the anchor 401 does not buckle and hits the tissue at the right angle. In this embodiment, the anchor 401 may have relatively more stiffness than in the embodiments where the anchors 401 are relatively flexible, in order to provide a more secure anchoring of the device 10 to the tissue. It is understood the tube 500 may provide this guiding function to the corresponding anchor in any of the embodiments described herein having moveable anchors, such as the moveable anchors 401, the anchors 120, etc.

The flexible anchors 401 and/or the external stiffening tube 500 may be made from biocompatible metallic materials such as Nitinol, implant grade stainless steel such as 304V or 316LVM, cobalt-chromium based alloys such as MP35N or Elgiloy, other suitable materials, or combinations thereof. The anchor 401 length can vary from 0.1 mm to 5 mm in length with an external stiffening tube 500 that covers from 10% to 90% of the exposed length of the anchor 401.

Figure 33:
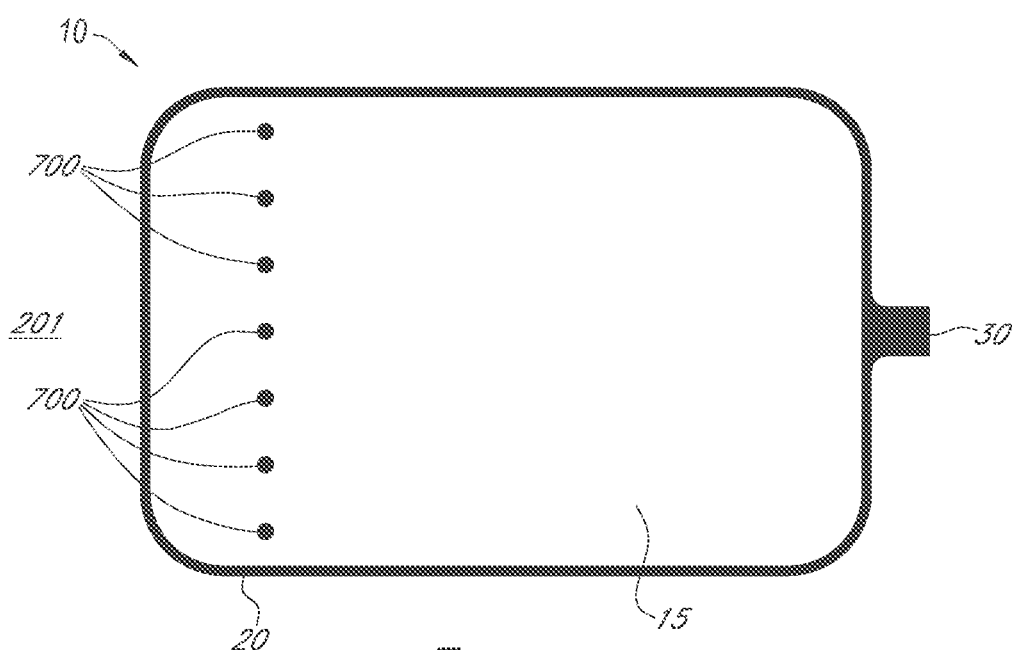
FIG. 33 is a side view of an embodiment of a device for occlusion of the LAA having discrete attachments of an outer skin to an internal foam.

The skin 20 at least partially surrounds the body 15 and portions of the skin 20 may or may not be attached to the body 15. The various devices 10 described herein may have the body 15 at least partially encased within the skin 20, which may be fabricated from a material such as ePTFE (expanded polytetrafluoroethylene), polyolefin, or polyester which assists with healing, anchoring, and retrieval. FIG. 33 is a side view of an embodiment of a device 10 for occlusion of the LAA having discrete points of attachment 700 of the skin 20 to the internal foam body 15. For clarity, the points of attachment 700 are shown as dots in the figures. It is understood the points of attachment 700 may not be visible from outside the device 10, for example the skin 20 may be bonded to the body 15 at the points of attachment 700, etc. In some embodiments, in addition or alternatively to bonding, the skin 20 may be secured for example with sutures to the body 15 at the points of attachment 700, and thus some or all of the points of attachment 700 may be visible from outside the device 10. The device 10 may be in the configuration shown in FIG. 33 adjacent to or within the left atrium (LA) 201. The skin 20 may be attached to the body 15 at the various separate points of attachment 700. As shown in FIG. 33, the skin 20 can be partially attached, with portions thereof not attached at all, to the body 15. This may allow, for example, the skin 20 to move during expansion of the body 15 that occurs after deployment of the device 10 from the delivery catheter. The skin 20 may, in some embodiments, be attached at points of attachment 700 located near the proximal side of the device 10, for example to help promote closure of the ostium of the LAA, such as with a rim 800 as described below. The skin 20 may, for example, be tacked in place in one or more points of attachment 700 near the proximal face so that any bunching of the skin 20 that occurs during implantation occurs near the ostium but within the LAA. This can be achieved using sutures, adhesive bonding, heat bonding, other suitable approaches, or combinations thereof.

Figure 34:
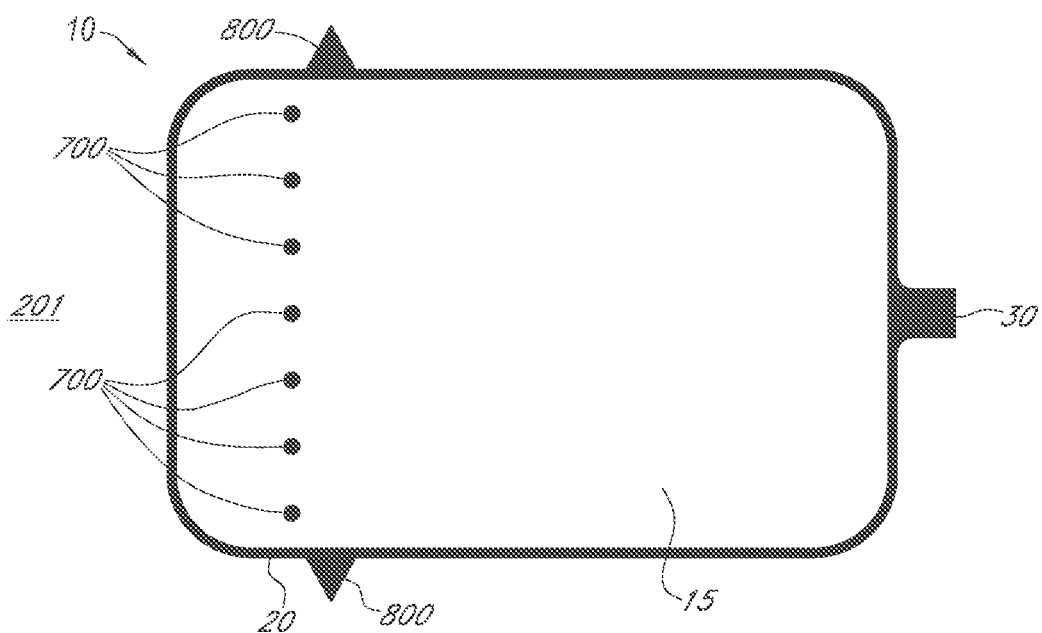
FIG. 34 is a side view of an embodiment of a device for occlusion of the LAA including an outer rim.

The selective location of the points of attachment 700 may facilitate with formation of a circumferential rim 800 of the skin 20. The rim 800 is shown schematically in FIG. 34 as a triangular rim for clarity. It is understood the rim 800 may be a variety of different shapes depending on the configuration of the device 10, the shape of the LAA, etc. Further, the rim 800 may extend completely or partially around the device 10. The rim 800 may surround the ostium of the LAA. The formation of the rim 800 may help to completely seal the entrance to the LAA around the device 10 and thereby prevent leakage. The attachment points 700 between the skin 20 and the body 15 can prevent irregular bunching of the fabric and instead guide any excess material to form the sealing rim 800 around or near the proximal face of the device 10, as shown in FIG. 34. The rim 800 may form upon expansion of the body 15 after deployment from the delivery catheter, as described herein. Alternatively the attachment points 700 can be designed so as to prevent any bunching at all of the fabric and provide a smooth surface, such as a smooth proximal surface.

Figure 35:
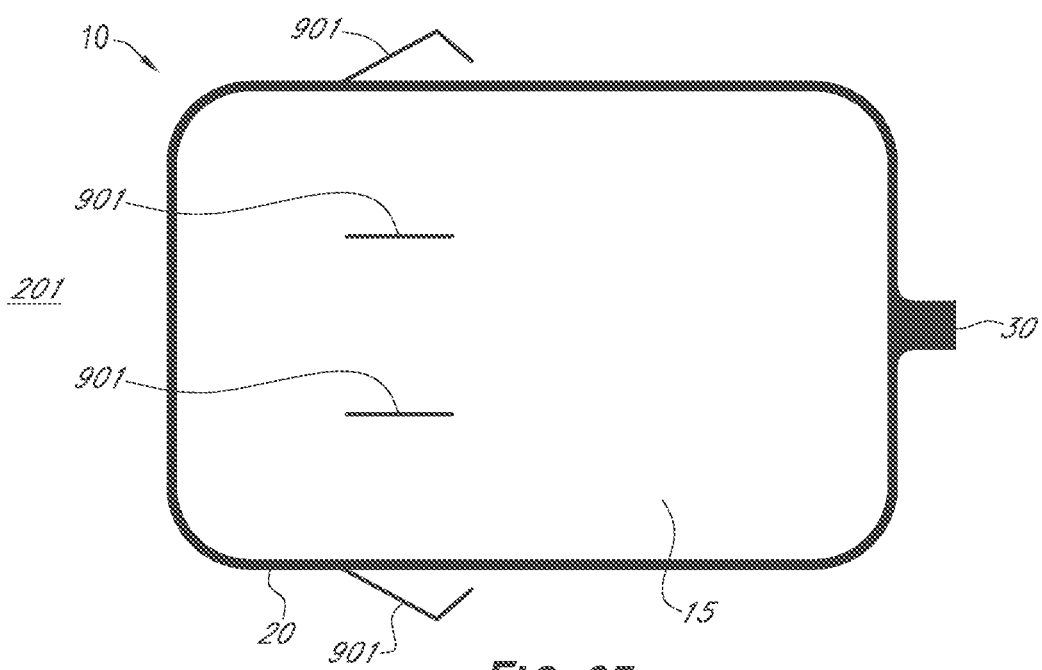
FIG. 35 is a side view of an embodiment of a device for occlusion of the LAA having anchors with V-tips shown in the deployed configuration.
Figure 36:
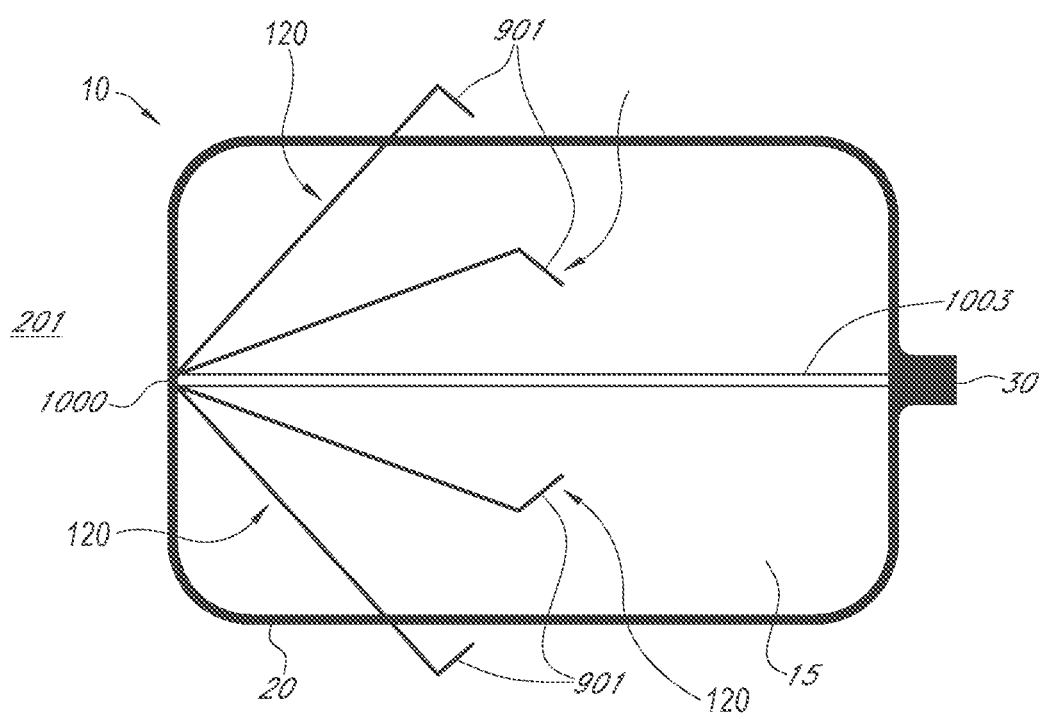
FIG. 36 is a side view of another embodiment of a device for occlusion of the LAA having anchors with V-tips shown in the deployed configuration.

FIGS. 35-36 are side views of embodiments of the device 10 having anchors 120 with V-tips 901 shown in the deployed configuration. The V-tips may be located in the proximal region 125 and/or may form all or part of the tissue engaging segment 121 of the anchor 120, as described herein. The V-tips 901 form a V-shaped point. The V-tips 901 are generally in the shape of a "V" or an otherwise angled, segmented shape. The V-tips 901 may be sharp barbs or hooks. The V-tips 901 may be formed from wire or laser-cut tubing or other suitable methods. As shown in FIG. 35, one or more of the V-tips 901 are attached to the body 15 encased in the skin 20. The V-tips 901 can be attached to the body 15 and/or to the skin 20. In some embodiments, the V-tips 901 are ends of anchors 1000. For example, the V-tips 901 may be part of the anchors 1000 that are within the body 15 and skin 20, as shown in FIG. 36. The distal ends of the V-tips 901 may be free to slide along and collapse or expand. The distal ends of the V-tips 901 may be attached to the body 15, skin 20, and/or the anchors 1000 to allow the V-tips 901 to collapse and retract. During retrieval into a catheter or sheath, the V-tips 901 can flatten out when engaging the inner diameter of the catheter or sheath. The V-tips 901 can be formed from Nitinol, implant grade stainless steel such as 304 or 316, cobalt-chromium based alloys such as MP35N or Elgiloy, other suitable materials, or combinations thereof. The V-tips 901 may then recover their pre-set shape after deployment or re-deployment.

Figure 37A:
FIGS. 37A-37C are side views of various embodiments of V-tips that may be used with the anchors described herein.
Figure 37B:
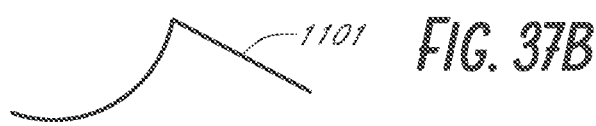
Figure 37C:
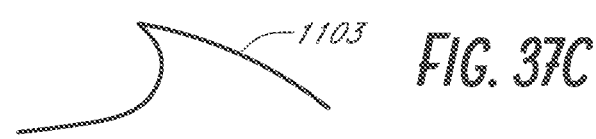

FIGS. 37A-37C are side views of various embodiments of V-tips that may be used with the anchors described herein. FIG. 37A is a side view of an embodiment of the V-tip 901. The V-tip 901 includes two angled segments. The segments may form the angle in a free state. The angle may be various angular amounts. In some embodiments, the angle formed by the V-tip 901 is no more than about 170°, 160°, 150°, 140°, 130°, 120°, 110°, 100°, 90°, 80°, 70°, 60°, or any smaller, greater or intermediate angular amount. FIG. 37B is a side view of an embodiment of a wave V-tip 1101. The wave V-tip 1101 may include a curved segment and an angled straight segment. FIG. 37C is a side view of an embodiment of a two-wave V-tip 1103. The two-wave V-tip 1103 may include two curved segments. The curved segments may promote engagement of the tip with the inner wall of the LAA. The end of the various V-tips may be smooth and rounded or sharp to promote tissue penetration. In some embodiments, all of the V-tips may have the same shape. In some embodiments, some of the V-tips may have a first shape and other V-tips may have a second shape different from the first shape. In some embodiments, some of the V-tips may be attached to the skin 20 and or body 15. In some embodiments, some of the V-tips may be attached to the anchors 1000.

Figure 38:
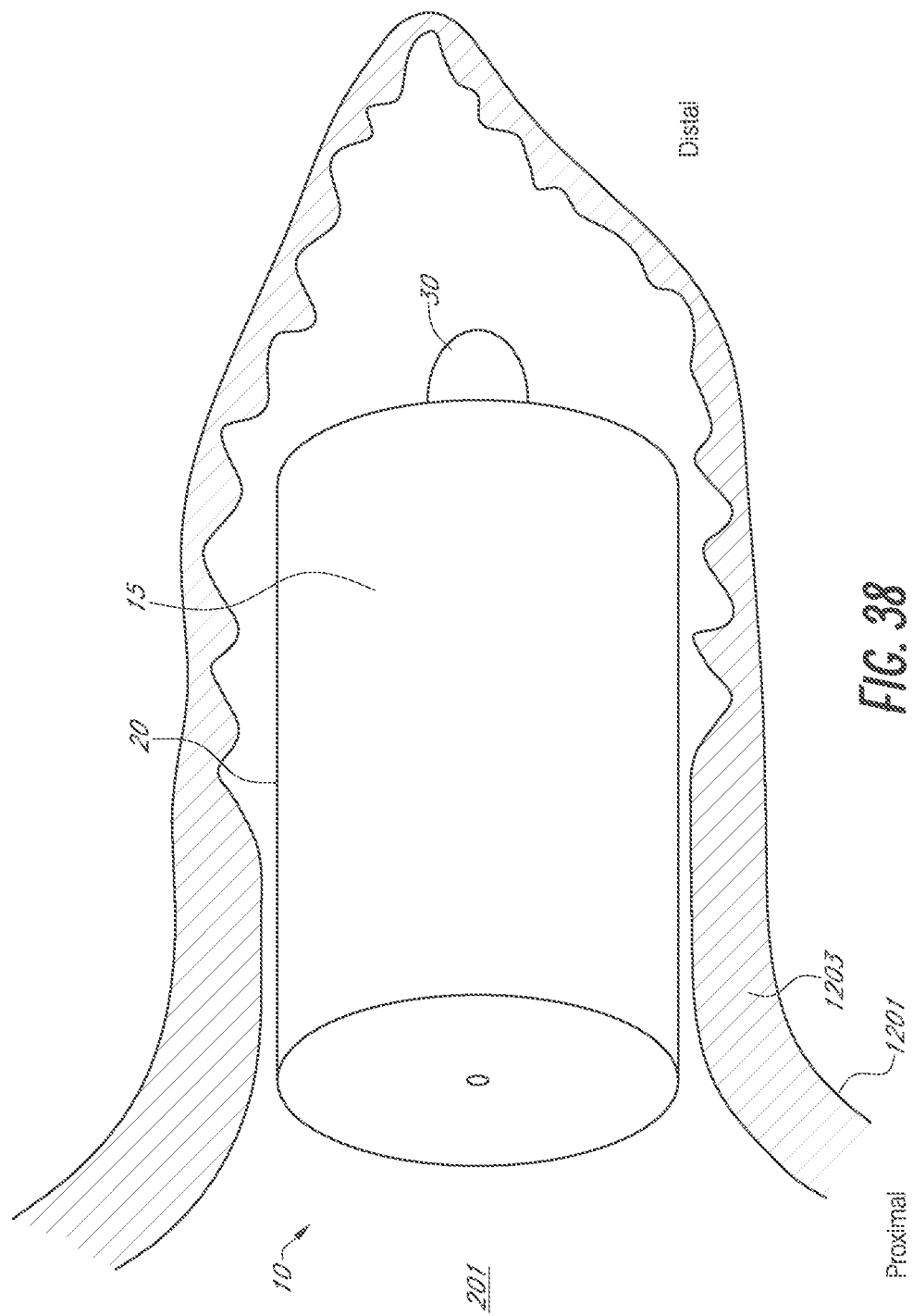
FIG. 38 is a side view of an embodiment of a device for occlusion of the LAA implanted inside an LAA.

FIG. 38 is a side view of an embodiment of a device 10 for occlusion of the LAA implanted inside an LAA 1201. The device 10 includes a body 15 with a skin 20 and finial 30 placed within the LAA 1201. The LAA includes a thicker proximal portion 1203 closer to the ostium. The internal locking system 101, for example anchors thereof, may be configured to engage with the thicker proximal portion 1203 of the LAA. The various anchors, V-tips etc. described herein for the various embodiments of the device 10 may be used to secure the anchors in the thicker proximal portion 1203. In some embodiments, the device 10 may be deployed from the catheter such that the body 15 expands. The location, orientation, etc. of the expanded body 15 within the LAA may be verified, for example by imaging, as described herein. The location, orientation, etc. of the expanded body 15 within the LAA may be verified to ensure engagement of the internal locking system 101, for example anchors thereof, with the thicker proximal portion 1203. Then, the internal locking system 101, for example anchors thereof, may be deployed to engage the thicker proximal portion 1203. If after deployment of the internal locking system 101, for example anchors thereof, it is determined that the anchors did not engage with the thicker proximal portion 1203, the anchors may be retracted, as described herein, in order to reposition and/or retrieve the device 10.

In some embodiments, the internal locking system 101, for example anchors thereof, may be preloaded surface elements releasably constrained or otherwise locked down in a collapsed or constrained position or configuration. The internal locking system 101, for example anchors thereof, may be constrained using a restraint. The restraint may be a dissolvable polymer, a lasso, or wires that can be retracted to release the anchors. The restraint may be similar to a deadbolt. Other anchoring concepts include Velcro integral to the ePTFE, electrically orientable/ratcheting anchoring elements, unidirectional Gecko tape, or wires pre-attached to the finial 30. In some embodiments, the body 15 with skin 20 may be secured within the LAA by texturing the body 15 and exposing the body 15 to the tissue through holes in the skin 20 to increase the friction with the cardiac surface to a high enough level to prevent implant migration.

Figure 39A:
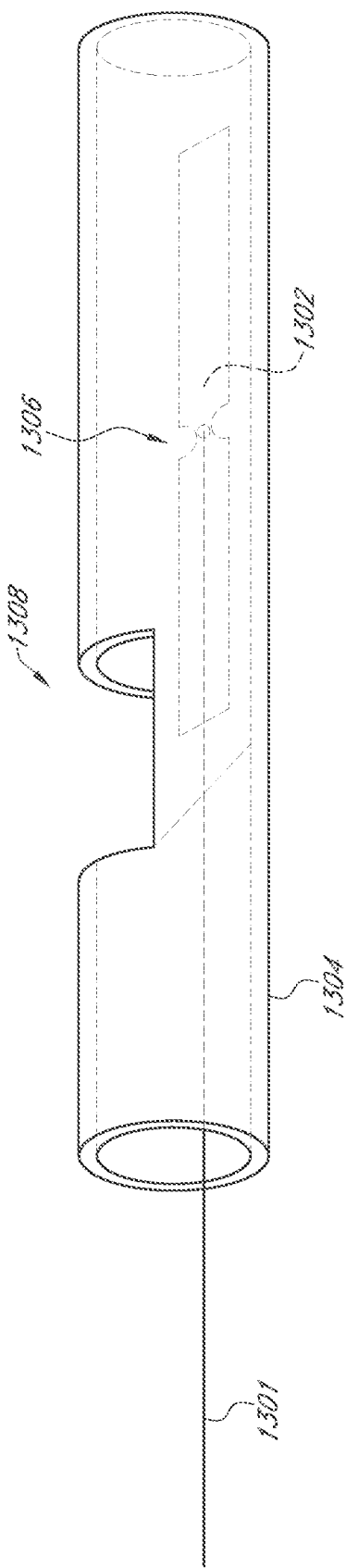
FIGS. 39A-39B are perspective views of an embodiment of a deployable anchor activated by a pull wire and shown, respectively, in the constrained and deployed configuration, that may be used with the various devices for occlusion of the LAA described herein.
Figure 39B:
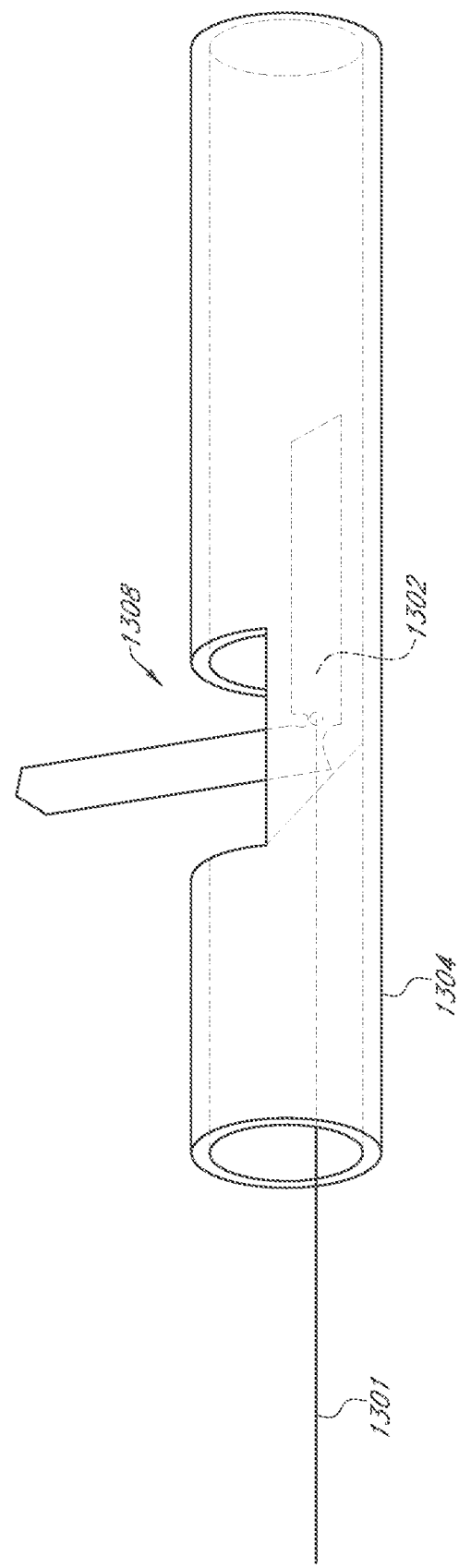

FIGS. 39A-39B are perspective views of an embodiment of a deployable anchor 1302 activated by a pull wire 1301 and shown, respectively, in the constrained and deployed configuration, that may be used with the various devices 10 for occlusion of the LAA described herein. A two-stage anchoring system allows deployment of the anchors 1302 after implantation and expansion of the body 15. This embodiment incorporates one or more hinged anchors 1302. The anchors 1302, which be a barb or other anchoring element, may lie flat during delivery and during deployment of the body 15. Next, when pulled or pushed, the anchors 1302 bend at a hinge 1306 and extend outward from the surface of the body 15 and into the LAA tissue. The anchors 1302 may bend at the hinge 1306 using a hollow constraining element 1304 which can be a thin, metallic, hollow round or rectangular box such as a round or rectangular shaped tube, and the pull wire 1301, for example a sliding element, which can be a wire or suture. The pull wire 1301 is attached to the proximal end of the anchor 1302 and extends back through the delivery catheter or sheath. When the pull wire 1301 is retracted, the anchor 1302 slides back though a slot 1308 in the tube 1304 and bends at the preformed hinge 1306. A portion of the anchor 1302 then extends out through the slot 1308.

FIGS. 40A-40B are perspective views of an embodiment of a deployable anchor 1405 activated by a lock wire 1401 and shown, respectively, in the constrained and deployed configuration, that may be used with the various devices 10 for occlusion of the LAA described herein. The anchor 1405, which be a barb or other anchoring element, may be formed from wire or a flat sheet of Nitinol or other shape memory material and heat set to be in an expanded configuration. One or more of the anchors 1405 can be placed along the skin 20 or otherwise along an external surface of the body 15. One or more corresponding guides 1402, such as loops, may be located along the skin 20 or the body 15. The guides 1402 may be located on both sides of the anchor 1405, as shown. The guides 1402 on a first side of the anchor 1405 may fix the anchors 1405 in place. The guides 1402 on a second, opposite side of the anchor 1405 may act as a guide for the lock wire 1401, which may be a restraining wire, suture, etc. The lock wire 1401 may be used to constrain the anchors 1405 in a constrained configuration, for example in the flat position as shown in FIG. 40A. When the lock wire 1401 is retracted, the anchors 1405 deploy, as shown in FIG. 40B. The anchors 1405 may extend perpendicular to the body 15, or at an angle.

Figure 41A:
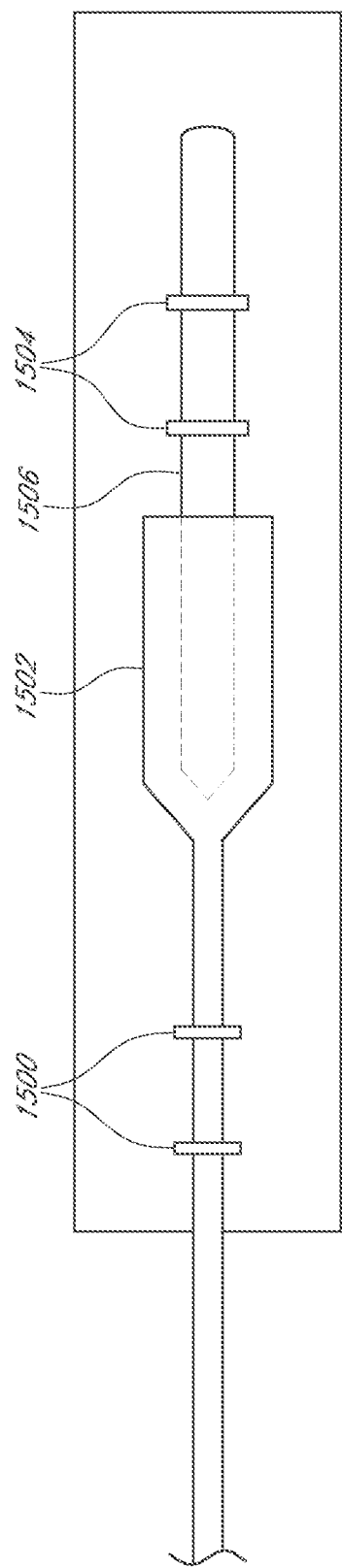
FIGS. 41A-41B are perspective views of an embodiment of a deployable anchor activated by a sheath and shown, respectively, in the constrained and deployed configuration, that may be used with the various devices for occlusion of the LAA described herein.
Figure 41B:
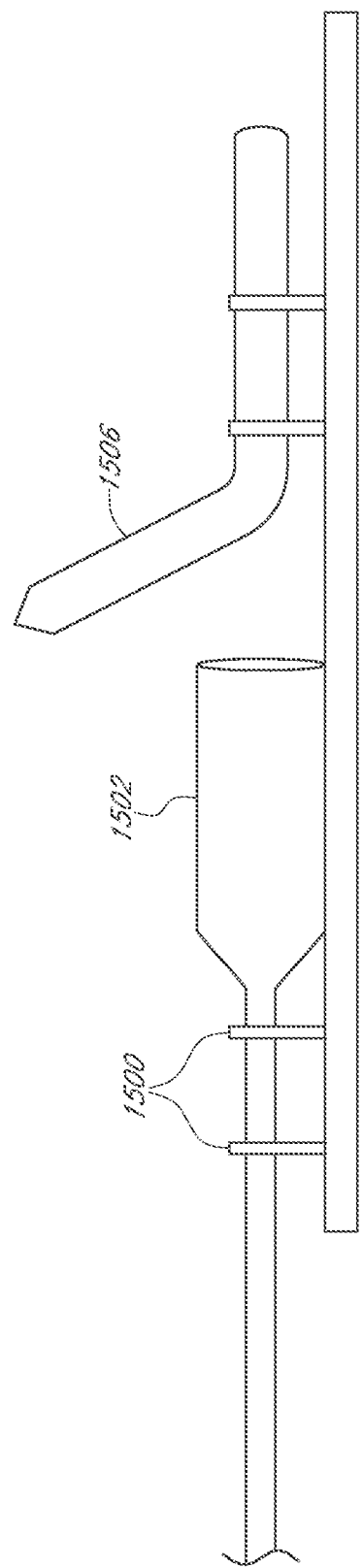

FIGS. 41A-41B are perspective views of an embodiment of a deployable anchor 1506 activated by a sheath 1502 and shown, respectively, in the constrained and deployed configuration, that may be used with the various devices for occlusion of the LAA described herein. The anchor 1506, which be a barb or other anchoring element, may be formed from wire or a flat sheet of Nitinol or other shape memory material and heat set to be in an expanded configuration.

One or more of the anchors 1506 may be placed along the skin 20 or otherwise along an external surface of the body 15. One or more corresponding guides 1500 and locking loops 1504 may be located along the skin 20 or the body 15. The guides 1500 may be located on a first side of the anchor 1506 and the locking loops 1504 may be located on a second, opposite side of the anchor 1506, as shown. The anchors 1506 are held in the constrained or restrained configuration or position by a sheath cover 1502. The sheath cover 1502 may be tubular or rectangular in shape. The sheath cover 1502 constrains the anchors 1506. The sheath cover 1502 may constrain the anchors 1506 in a flat position as shown in FIG. 41A. When the sheath cover 1502 is retracted, the anchors 1506 deploy, as shown in FIG. 41B. The anchors 1506 may extend at an angle to the body 15, or perpendicularly.

Figure 42B:
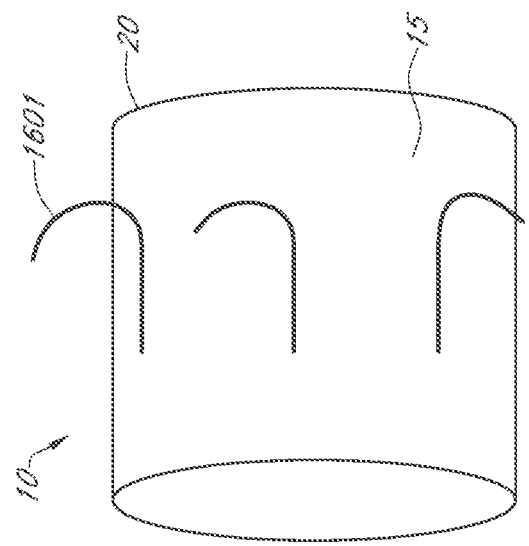
FIGS. 42A-42D are various views of embodiments of devices for occlusion of the LAA having external deployable anchors which can be collapsed and expanded by retraction into or out of a sheath or outer catheter.
Figure 42A:
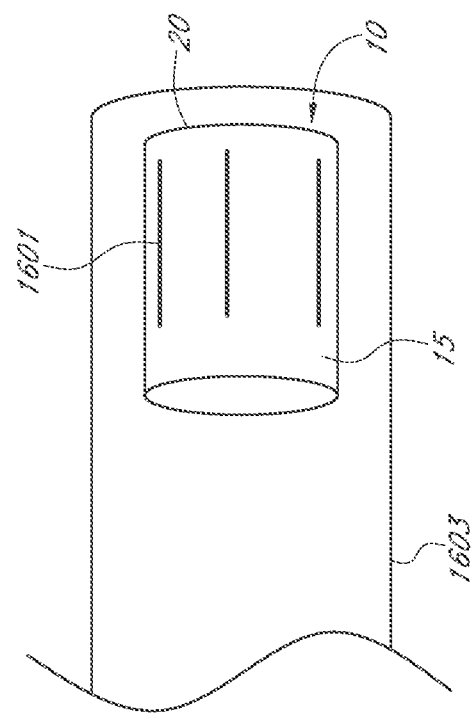
Figure 42D:
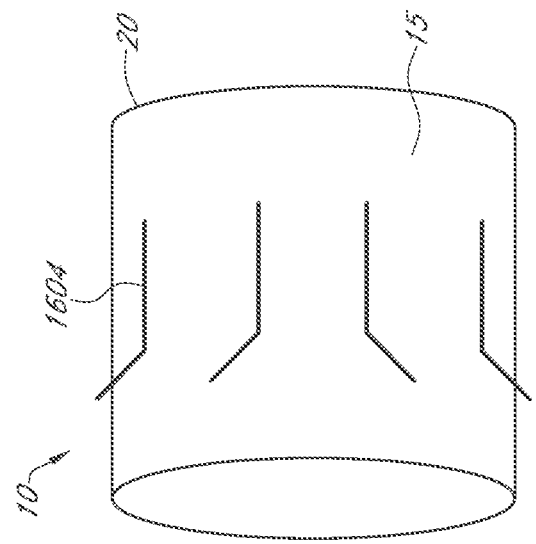
Figure 42C:
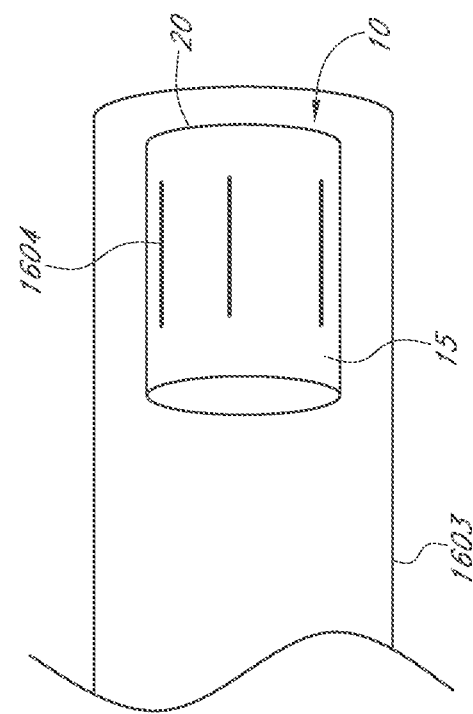

FIGS. 42A-42D are various views of embodiments of devices 10 for occlusion of the LAA having external deployable anchors 1601, 1604 which can be collapsed and expanded by retraction into or out of a sheath or outer catheter. FIG. 42A is a side view of the device 10 having anchors 1601 constrained by a delivery sheath 1603. FIG. 42B is a side view of the device 10 unconstrained by the delivery sheath 1603 with the anchors 1601 deployed. FIG. 42C is a side view of the device 10 having anchors 1604 constrained by the delivery sheath 1603. FIG. 42D is a side view of the device 10 unconstrained by the delivery sheath 1603 with the anchors 1604 deployed. The body 15 with skin 20 can contain the anchors 1601 or 1604 which are fixed to the surface of the skin 20 and are unconstrained and therefore expanded in a free state, as shown in FIGS. 42B and 42D. The delivery sheath 1603, such as a catheter, may be used to constrain the anchors 1601 or 1604. The anchors 1601 or 1604 may then expand when the body 15 is unconstrained by the delivery sheath 1603, for example when the when the body 15 is released from the delivery sheath 1603. The anchors 1601 may deploy into a curved shape as shown in FIG. 42B. The anchors 1604 may deploy into an angled shape as shown in FIG. 42D. The anchors 1603 or 1604 after deployment may point toward either the proximal or distal side of the body 15.

Figure 43A:
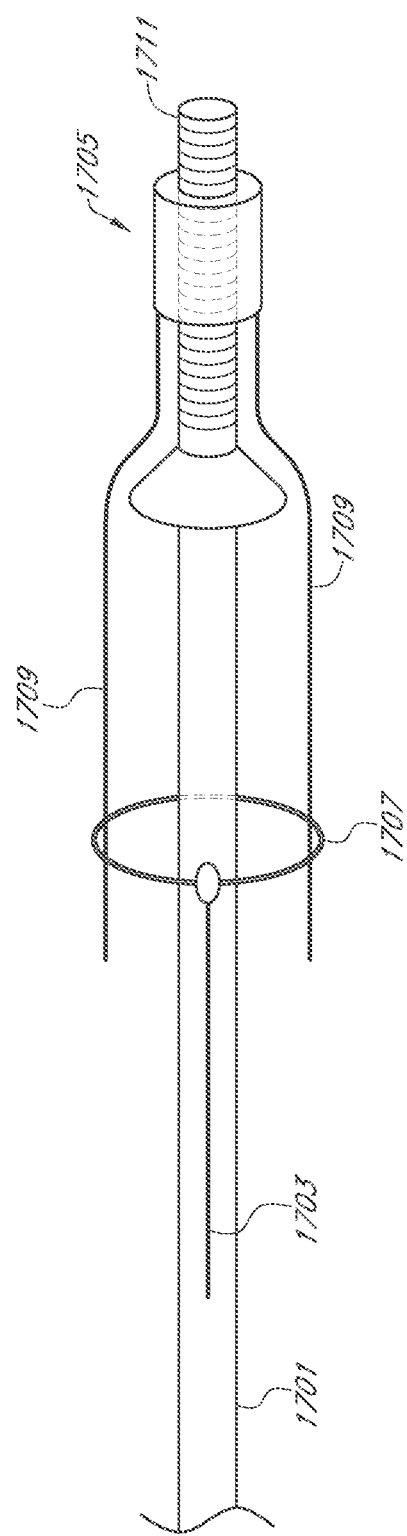
Figure 43C:
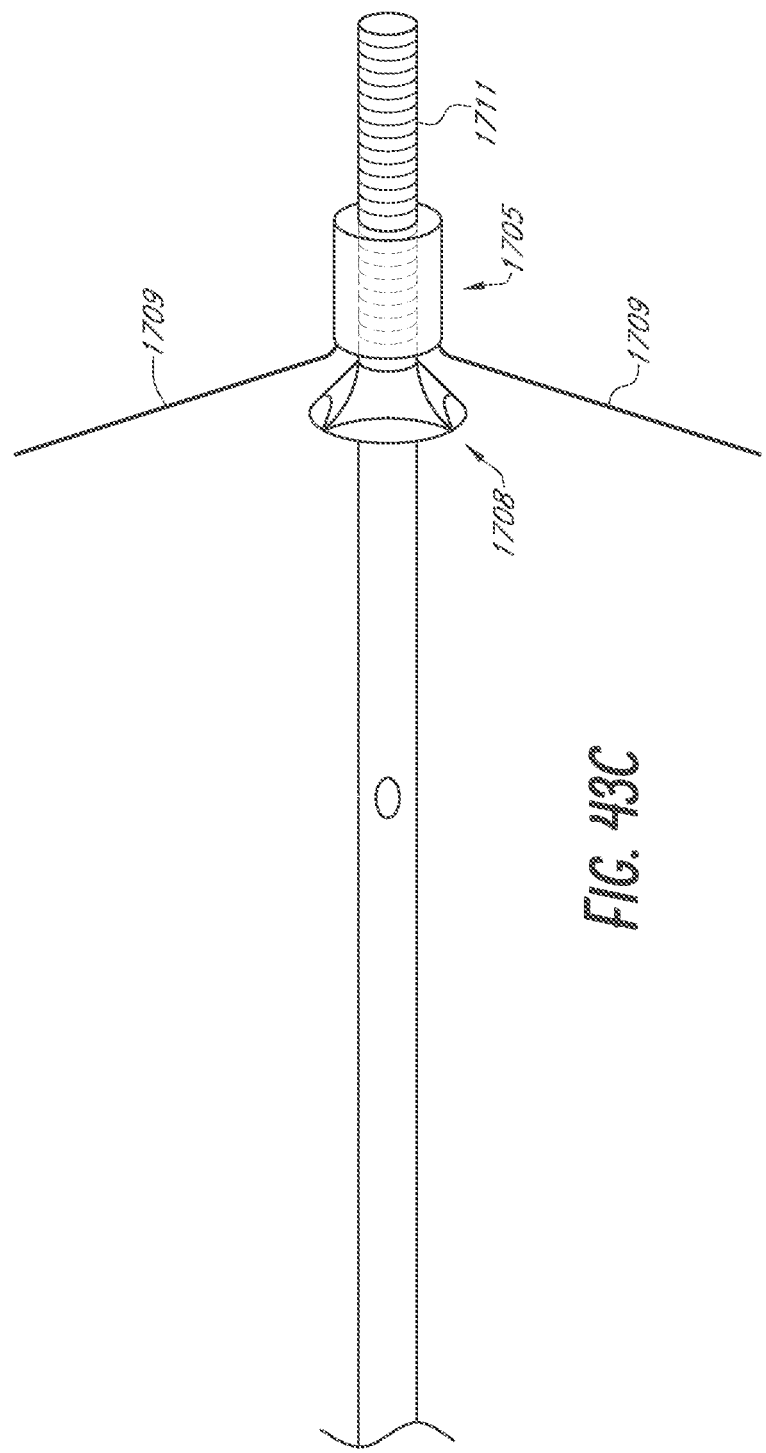

FIGS. 43A-43C are sequential side views of an embodiment of a device 10 for occlusion of the LAA shown, respectively, constrained by a lasso 1707, deployed, and adjusted with a mount 1705. One or more anchors 1709 may be pre-mounted within the body 15 and attached distally to the mount 1705. The mount 1705 may be a ring-like member having an opening extending therethrough. The mount 1705 is positioned over a 1701 rod 1711. The mount 1705 can move, for example slide, over the 1701 rod 1711 in the proximal direction. In some embodiments, the mount 1705 may be pulled proximally, for example by a pull wire. In some embodiments, the mount 1705 may move when the 1701 rod 1711 is rotated. In some embodiments, the mount 1705 and/or 1701 rod 1711 may be threaded. Movement of the mount 1705 causes the anchor 1705 to move. The device may include a tapered cone 1708. The cone 1708 may be attached to the end of the rod 1711. The mount 1705 may be moved toward the cone 1708 to adjust the height of the anchors 1709. Thus, the anchors 1709 are angled more in FIG. 17C relative to FIG. 17B. The anchor 1709 may move through the body 15 and into the tissue. The anchors 1709 may be adjusted to increase or decrease the amount of tissue penetration, for example by moving the mount 1705 as described. For retrieval, this process can be reversed. In some embodiments, the lasso 1707, attached to a wire 1703, may extend, for example thread, through the threaded 1701 rod 1711 and be placed around the anchors 1709 to retract the anchors 1709 back into the body 15. In some embodiments, the lasso 1707 may be used to initially constrain the anchors 1709 and then retract to allow the anchors 1709 to deploy.

Figure 44C:
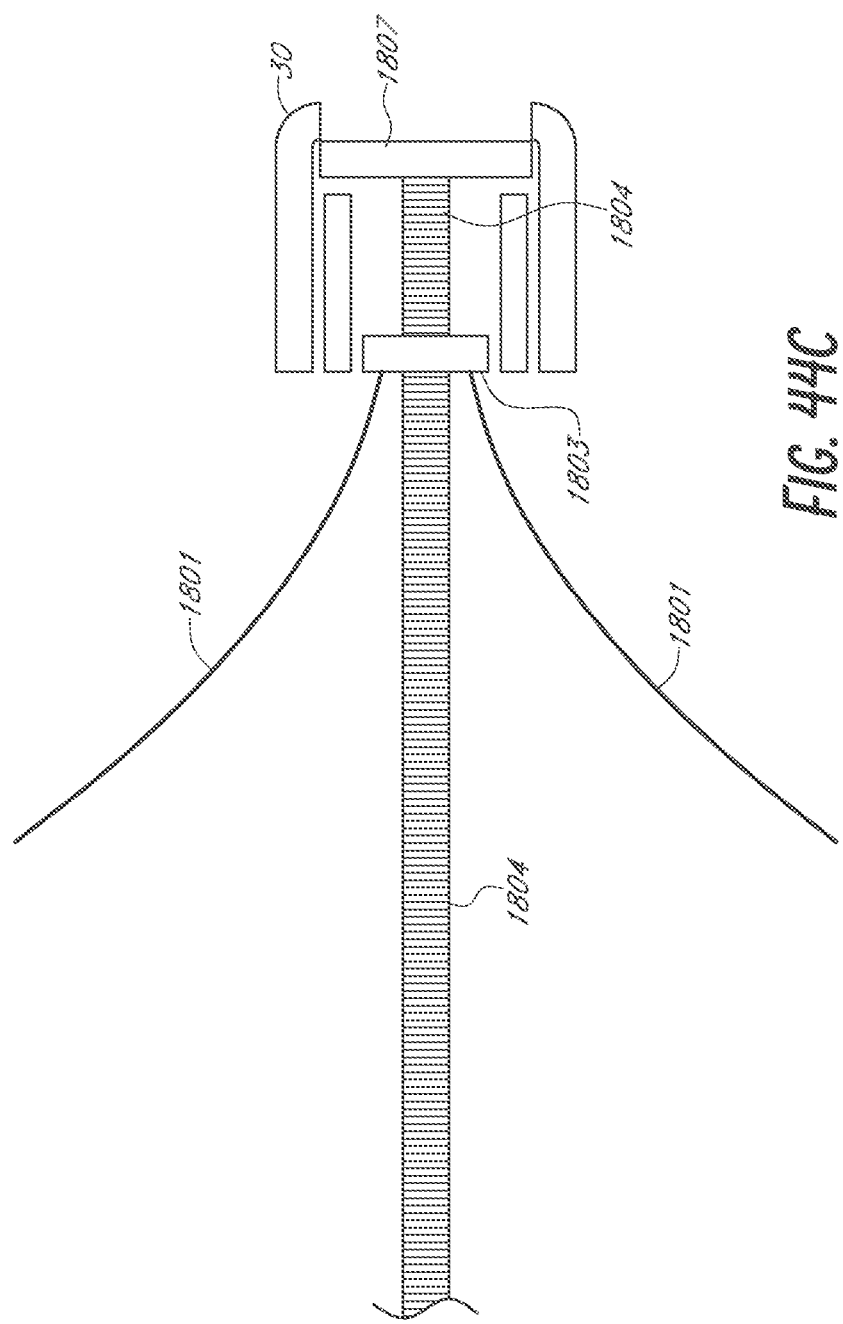

FIGS. 44A-44C are side views of an embodiment of a device 10 for occlusion of the LAA having an adjustable two stage anchor system with anchors 1801 activated by moving a mount 1803 along a rod 1804. The anchors 1801 may be internal grappling hook type structures placed within the body 15 and skin 20. The anchors 1801 may be introduced through a central lumen 1003 that extends through the body 15, as shown in FIG. 43A. The anchors 1801 may then travel through the body 15 and skin 20 to engage tissue, as shown in FIG. 43B. The anchors 1801 may be adjusted to increase or decrease the amount of tissue penetration. The anchors 1801 are attached at distal ends to the moveable mount 1803. The mount 1803 is prevented from rotating, for example the mount 1803 may be notched to prevent rotation of the mount 1803 within the finial 30, as shown in FIG. 43C. The mount 1803 is threaded onto the threaded rod 1804 that can be rotated clockwise or counter clockwise to change the linear position of the mount 1803. The distal end of the rod 1804 may couple with a cap 1807. The cap 1807 may rotate with the rotation of the rod 1804. The mount 1803 may move proximally causing the anchors 1801 to extend past the surface of the body 15 and skin 20 as shown in FIG. 43B. The mount 1803 may move distally to pull the anchors 1801 back within or under the surface of the skin 20. The depth of penetration of the anchors 1801 may be controlled, for example to account for the non-circular cross-section of the LAA. In some embodiments, the anchors 1801 may be deployed individually. Another option is to deploy the anchors 1801 distal to the body 15 with skin 20 and control the stiffness of the anchors 1801 such that they apply a reasonably uniform penetrating force to the tissue at contact.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method of excluding a left atrial appendage (LAA), the method comprising:
   advancing a guidewire into the LAA;
   advancing a distal end of a delivery catheter over the guidewire and into the LAA;
   deploying a LAA occlusion device from the distal end of the delivery catheter, wherein the LAA occlusion device includes a foam body and a support structure having an anchor; and
   engaging tissue of the LAA with the anchor to secure the LAA occlusion device within the LAA, wherein the anchor penetrates the foam body such that a tip of the anchor is positioned outside the foam body to engage the tissue.

2. The method of claim 1, wherein the anchor extends along an axis, and the method further comprises advancing the anchor along the axis to engage the tissue.

3. The method of claim 1, further comprising rotating the anchor to engage the tissue with the anchor.

4. The method of claim 1, further comprising deploying the anchor from a constrained configuration to a deployed configuration.

5. The method of claim 1, further comprising:
   compressing the LAA occlusion device to a constrained configuration for delivery; and
   expanding the LAA occlusion device to a deployed configuration after deploying the LAA occlusion device from the delivery catheter.

6. The method of claim 5, wherein expanding the LAA occlusion device comprises the LAA occlusion device self-expanding after deploying from the delivery catheter.

7. The method of claim 5, further comprising restraining the LAA occlusion device with a sheath for delivery.

8. The method of claim 7, further comprising removing the sheath from the LAA occlusion device.

9. The method of claim 8, wherein expanding the LAA occlusion device comprises the LAA occlusion device self-expanding after removal of the sheath.

10. The method of claim 1, further comprising retracting the anchor from engagement with the tissue.

11. The method of claim 10, further comprising repositioning the LAA occlusion device after retracting the anchor.

12. The method of claim 11, further comprising re-engaging the tissue with the anchor after repositioning the LAA occlusion device.

13. The method of claim 1, wherein the LAA occlusion device comprises a plurality of the anchors, and the method further comprises engaging the tissue with the plurality of anchors.

14. The method of claim 13, wherein the plurality of the anchors penetrate the foam body such that respective tips of the plurality of anchors are positioned outside the foam body to engage the tissue.

15. The method of claim 1, wherein deploying the LAA occlusion device comprises retracting a sheath distally from around the LAA occlusion device to allow the LAA occlusion device to self-expand.

16. The method of claim 15, further comprising re-sheathing the LAA occlusion device after expansion of the LAA occlusion device.

17. The method of claim 1, wherein the foam body comprises a proximal face and a sidewall extending distally from the proximal face.

18. The method of claim 1, wherein the support structure comprises a central hub and the anchor is connected to the hub via a support segment.

19. The method of claim 1, wherein the support structure comprises a plurality of struts joined at a distal end to a central hub.

20. The method of claim 1, wherein a proximal end of the LAA occlusion device faces the left atrium after delivery and comprises a thromboresistant blood-contacting surface.

* * * * *

UNITED STATES PATENT AND TRADEMARK OFFICE
CERTIFICATE OF CORRECTION

PATENT NO. : 11,399,842 B2
APPLICATION NO. : 16/846076
DATED : August 2, 2022
INVENTOR(S) : Aaron V. Kaplan et al.

It is certified that error appears in the above-identified patent and that said Letters Patent is hereby corrected as shown below:

On the Title Page

Page 2, Column 1 (Related U.S. Application Data), Line 4, Delete "2015." and insert -- 2015, provisional application No. 61/779,802, filed on Mar. 13, 2013. --.

Signed and Sealed this
Fourteenth Day of March, 2023

Katherine Kelly Vidal
*Director of the United States Patent and Trademark Office*